United States Patent
Hong et al.

(10) Patent No.: US 10,216,893 B2
(45) Date of Patent: Feb. 26, 2019

(54) MULTIMODE SENSOR DEVICES

(71) Applicant: Fitbit, Inc., San Francisco, CA (US)

(72) Inventors: Jung Ook Hong, Emeryville, CA (US); Andrew Cole Axley, Oakland, CA (US); Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/216,743

(22) Filed: Mar. 17, 2014

(65) Prior Publication Data

US 2014/0303523 A1    Oct. 9, 2014

Related U.S. Application Data

(63) Continuation-in-part of application No. 13/156,304, filed on Jun. 8, 2011, now Pat. No. 9,167,991.
(Continued)

(51) Int. Cl.
*G06F 19/10*    (2011.01)
*A61B 5/11*    (2006.01)
(Continued)

(52) U.S. Cl.
CPC ............ *G06F 19/10* (2013.01); *A61B 5/0205* (2013.01); *A61B 5/112* (2013.01); *A61B 5/1112* (2013.01);
(Continued)

(58) Field of Classification Search
CPC ...... A61B 5/4528; A61B 5/1071; A61B 5/103
(Continued)

(56) References Cited

U.S. PATENT DOCUMENTS 4,367,752 A    1/1983    Jimenez et al.
4,771,792 A *  9/1988    Seale ............................ 600/587
(Continued)

FOREIGN PATENT DOCUMENTS

CN    1623175 A    6/2005
CN    101615098 A    12/2009
(Continued)

OTHER PUBLICATIONS

"Activator is One of the Best Cydia iPhone Hacks | Control your iPhone with Gestures," iphone-tips-and-advice.com, [retrieved on Jul. 9, 2013 at http://www.iphone-tips-and-advice.com/activatior. html], 10 pp.
(Continued)

*Primary Examiner* — Daniel L Cerioni
(74) *Attorney, Agent, or Firm* — Weaver Austin Villeneuve & Sampson LLP

(57) ABSTRACT

The disclosure provides BMDs that have multiple device modes depending on operational conditions of the devices, e.g., motion intensity, device placement, and/or activity type, the device modes are associated with various data processing algorithms. In some embodiments, the BMD is implemented as a wrist-worn or arm-worn device. In some embodiments, methods for tracking physiological metrics using the BMDs are provided. In some embodiments, the process and the BMD applies a time domain analysis on data provided by a sensor of the BMD when the data has a high signal (e.g., high signal-to-noise ratio), and applies a frequency domain analysis on the data when the data has a low signal, which contributes to improved accuracy and speed of biometric data.

20 Claims, 12 Drawing Sheets

Related U.S. Application Data

(60) Provisional application No. 61/800,095, filed on Mar. 15, 2013, provisional application No. 61/388,595, filed on Sep. 30, 2010, provisional application No. 61/390,811, filed on Oct. 7, 2010.

(51) Int. Cl.
  *A61B 5/00* (2006.01)
  *A61B 5/0205* (2006.01)
  *G01C 22/00* (2006.01)
  *G06F 19/00* (2018.01)
  *A61B 5/024* (2006.01)

(52) U.S. Cl.
  CPC .......... *A61B 5/1118* (2013.01); *A61B 5/1121* (2013.01); *A61B 5/1123* (2013.01); *A61B 5/4815* (2013.01); *A61B 5/4866* (2013.01); *A61B 5/681* (2013.01); *A61B 5/6824* (2013.01); *A61B 5/721* (2013.01); *A61B 5/725* (2013.01); *A61B 5/726* (2013.01); *A61B 5/7207* (2013.01); *A61B 5/7235* (2013.01); *A61B 5/7257* (2013.01); *A61B 5/7264* (2013.01); *A61B 5/7282* (2013.01); *G01C 22/006* (2013.01); *A61B 5/024* (2013.01); *A61B 5/7221* (2013.01); *A61B 5/7253* (2013.01); *G06F 19/3481* (2013.01)

(58) Field of Classification Search
  USPC .................................................. 600/587, 595
  See application file for complete search history.

(56) References Cited

U.S. PATENT DOCUMENTS

| | | | |
|---|---|---|---|
| 4,781,195 A | 11/1988 | Martin | |
| 5,036,856 A | 8/1991 | Thornton | |
| 5,101,831 A | 4/1992 | Koyama et al. | |
| 5,318,597 A | 6/1994 | Hauck et al. | |
| 5,738,104 A | 4/1998 | Lo et al. | |
| 5,954,644 A | 9/1999 | Dettling et al. | |
| 6,076,015 A | 6/2000 | Hartley et al. | |
| 6,099,478 A | 8/2000 | Aoshima et al. | |
| 6,131,076 A | 10/2000 | Stephan et al. | |
| 6,241,684 B1 | 6/2001 | Amano et al. | |
| 6,289,230 B1 | 9/2001 | Chaiken et al. | |
| 6,307,576 B1 | 10/2001 | Rosenfeld | |
| 6,402,690 B1 | 6/2002 | Rhee et al. | |
| 6,418,394 B1 | 7/2002 | Puolakanaho et al. | |
| 6,583,369 B2 | 6/2003 | Montagnino et al. | |
| 6,585,622 B1 | 7/2003 | Shum et al. | |
| 6,731,967 B1 | 5/2004 | Turcott | |
| 6,882,955 B1 | 4/2005 | Ohlenbusch et al. | |
| 6,959,259 B2 | 10/2005 | Vock et al. | |
| 6,997,882 B1* | 2/2006 | Parker et al. | 600/534 |
| 7,020,508 B2 | 3/2006 | Stivoric et al. | |
| 7,153,262 B2 | 12/2006 | Stivoric et al. | |
| 7,171,331 B2 | 1/2007 | Vock et al. | |
| 7,285,090 B2 | 10/2007 | Stivoric et al. | |
| 7,334,472 B2 | 2/2008 | Seo et al. | |
| 7,539,532 B2 | 5/2009 | Tran | |
| 7,579,946 B2 | 8/2009 | Case, Jr. | |
| 7,720,306 B2* | 5/2010 | Gardiner et al. | 382/276 |
| 7,909,768 B1 | 3/2011 | Turcott | |
| 7,993,276 B2 | 8/2011 | Nazarian et al. | |
| 8,040,758 B1 | 10/2011 | Dickinson | |
| 8,073,707 B2 | 12/2011 | Teller et al. | |
| 8,109,858 B2 | 2/2012 | Redmann | |
| 8,140,143 B2 | 3/2012 | Picard et al. | |
| 8,152,745 B2 | 4/2012 | Smith et al. | |
| 8,157,731 B2 | 4/2012 | Teller et al. | |
| 8,172,761 B1 | 5/2012 | Rulkov et al. | |
| 8,199,126 B1 | 6/2012 | Taubman | |
| 8,211,503 B2 | 7/2012 | Tsao et al. | |
| 8,346,328 B2 | 1/2013 | Mannheimer et al. | |
| 8,386,042 B2 | 2/2013 | Yudovsky et al. | |
| 8,398,546 B2 | 3/2013 | Pacione et al. | |
| 8,444,578 B2 | 5/2013 | Bourget et al. | |
| 8,446,275 B2 | 5/2013 | Utter, II | |
| 8,475,367 B1 | 7/2013 | Yuen et al. | |
| 8,579,827 B1 | 11/2013 | Rulkov et al. | |
| 8,641,612 B2 | 2/2014 | Teller et al. | |
| 8,742,325 B1 | 6/2014 | Droz et al. | |
| 8,792,981 B2 | 7/2014 | Yudovsky et al. | |
| 8,868,377 B2 | 10/2014 | Yuen et al. | |
| 8,909,543 B2 | 12/2014 | Tropper et al. | |
| 8,920,332 B2 | 12/2014 | Hong et al. | |
| 8,936,552 B2 | 1/2015 | Kateraas et al. | |
| 8,945,017 B2 | 2/2015 | Venkatraman et al. | |
| 8,948,832 B2 | 2/2015 | Hong et al. | |
| 8,954,135 B2 | 2/2015 | Yuen et al. | |
| 8,956,303 B2 | 2/2015 | Hong et al. | |
| 8,961,413 B2 | 2/2015 | Teller et al. | |
| 8,998,815 B2 | 4/2015 | Venkatraman et al. | |
| 9,005,129 B2 | 4/2015 | Venkatraman et al. | |
| 9,031,812 B2 | 5/2015 | Roberts et al. | |
| 9,042,971 B2 | 5/2015 | Brumback et al. | |
| 9,044,149 B2 | 6/2015 | Richards et al. | |
| 9,044,150 B2 | 6/2015 | Brumback et al. | |
| 9,049,998 B2 | 6/2015 | Brumback et al. | |
| 9,089,760 B2 | 7/2015 | Tropper et al. | |
| 9,113,794 B2 | 8/2015 | Hong et al. | |
| 9,113,795 B2 | 8/2015 | Hong et al. | |
| 9,226,663 B2 | 1/2016 | Fei | |
| 9,237,855 B2 | 1/2016 | Hong et al. | |
| 9,282,902 B2 | 3/2016 | Richards et al. | |
| 9,307,917 B2 | 4/2016 | Hong et al. | |
| 9,392,946 B1 | 7/2016 | Sarantos et al. | |
| 9,402,552 B2 | 8/2016 | Richards et al. | |
| 9,456,787 B2 | 10/2016 | Venkatraman et al. | |
| 9,662,053 B2 | 5/2017 | Richards et al. | |
| 2001/0044588 A1 | 11/2001 | Mault | |
| 2002/0139936 A1 | 10/2002 | Dumas | |
| 2003/0107487 A1 | 6/2003 | Korman et al. | |
| 2003/0163710 A1 | 8/2003 | Ortiz et al. | |
| 2004/0171969 A1 | 9/2004 | Socci et al. | |
| 2004/0236227 A1 | 11/2004 | Gueissaz | |
| 2005/0020927 A1 | 1/2005 | Blondeau et al. | |
| 2005/0054940 A1 | 3/2005 | Almen | |
| 2005/0245793 A1 | 11/2005 | Hilton et al. | |
| 2005/0253047 A1 | 11/2005 | Maegawa et al. | |
| 2006/0052727 A1 | 3/2006 | Palestrant | |
| 2006/0195020 A1* | 8/2006 | Martin et al. | 600/301 |
| 2007/0213020 A1 | 9/2007 | Novac | |
| 2007/0219059 A1 | 9/2007 | Schwartz et al. | |
| 2007/0265533 A1 | 11/2007 | Tran | |
| 2008/0039729 A1 | 2/2008 | Cho et al. | |
| 2008/0097221 A1 | 4/2008 | Florian | |
| 2008/0214360 A1 | 9/2008 | Stirling et al. | |
| 2008/0214903 A1 | 9/2008 | Orbach | |
| 2009/0012433 A1 | 1/2009 | Fernstrom et al. | |
| 2009/0132197 A1 | 5/2009 | Rubin et al. | |
| 2009/0163783 A1 | 6/2009 | Mannheimer et al. | |
| 2009/0292332 A1 | 11/2009 | Li et al. | |
| 2009/0318779 A1 | 12/2009 | Tran | |
| 2010/0026995 A1 | 2/2010 | Merritt et al. | |
| 2010/0063365 A1 | 3/2010 | Pisani et al. | |
| 2010/0079291 A1 | 4/2010 | Kroll et al. | |
| 2010/0106044 A1 | 4/2010 | Linderman | |
| 2010/0152600 A1 | 6/2010 | Droitcour et al. | |
| 2010/0204550 A1 | 8/2010 | Heneghan et al. | |
| 2010/0249633 A1 | 9/2010 | Droitcour et al. | |
| 2010/0274100 A1 | 10/2010 | Behar et al. | |
| 2010/0292568 A1 | 11/2010 | Droitcour et al. | |
| 2010/0298650 A1 | 11/2010 | Moon et al. | |
| 2010/0298651 A1 | 11/2010 | Moon et al. | |
| 2010/0298653 A1 | 11/2010 | McCombie et al. | |
| 2010/0298661 A1* | 11/2010 | McCombie et al. | 600/301 |
| 2010/0331145 A1 | 12/2010 | Lakovic et al. | |
| 2010/0331657 A1 | 12/2010 | Mensinger et al. | |
| 2011/0009727 A1 | 1/2011 | Mensinger et al. | |
| 2011/0032105 A1 | 2/2011 | Hoffman et al. | |
| 2011/0066010 A1 | 3/2011 | Moon et al. | |

(56) References Cited

U.S. PATENT DOCUMENTS

| | | | |
|---|---|---|---|
| 2011/0112442 A1* | 5/2011 | Meger | A61B 5/0002 600/595 |
| 2011/0118621 A1 | 5/2011 | Chu | |
| 2011/0237912 A1 | 9/2011 | Couronne et al. | |
| 2011/0276304 A1 | 11/2011 | Yin et al. | |
| 2012/0083705 A1* | 4/2012 | Yuen et al. | 600/508 |
| 2012/0083714 A1 | 4/2012 | Yuen et al. | |
| 2012/0083715 A1 | 4/2012 | Yuen et al. | |
| 2012/0083716 A1 | 4/2012 | Yuen et al. | |
| 2012/0084053 A1 | 4/2012 | Yuen et al. | |
| 2012/0084054 A1 | 4/2012 | Yuen et al. | |
| 2012/0123232 A1 | 5/2012 | Najarian et al. | |
| 2012/0143067 A1 | 6/2012 | Watson et al. | |
| 2012/0150074 A1 | 6/2012 | Yanev et al. | |
| 2012/0172733 A1 | 7/2012 | Park | |
| 2012/0226471 A1 | 9/2012 | Yuen et al. | |
| 2012/0226472 A1 | 9/2012 | Yuen et al. | |
| 2012/0232432 A1 | 9/2012 | Kahn et al. | |
| 2012/0245439 A1 | 9/2012 | Andre et al. | |
| 2012/0253486 A1 | 10/2012 | Niemimaki | |
| 2012/0255875 A1 | 10/2012 | Vicente et al. | |
| 2012/0271180 A1 | 10/2012 | Ren et al. | |
| 2012/0274508 A1 | 11/2012 | Brown et al. | |
| 2012/0316471 A1 | 12/2012 | Rahman et al. | |
| 2013/0009779 A1 | 1/2013 | Wittling et al. | |
| 2013/0053661 A1 | 2/2013 | Alberth et al. | |
| 2013/0073254 A1 | 3/2013 | Yuen et al. | |
| 2013/0073255 A1 | 3/2013 | Yuen et al. | |
| 2013/0077823 A1 | 3/2013 | Mestha et al. | |
| 2013/0077826 A1 | 3/2013 | Cowperthwaite et al. | |
| 2013/0079607 A1 | 3/2013 | Gareau et al. | |
| 2013/0080113 A1 | 3/2013 | Yuen et al. | |
| 2013/0106684 A1 | 5/2013 | Weast et al. | |
| 2013/0151196 A1 | 6/2013 | Yuen et al. | |
| 2013/0158369 A1 | 6/2013 | Yuen et al. | |
| 2013/0173171 A1 | 7/2013 | Drysdale et al. | |
| 2013/0191034 A1* | 7/2013 | Weast | G06F 17/00 702/19 |
| 2013/0211265 A1 | 8/2013 | Bedingham et al. | |
| 2013/0218053 A1* | 8/2013 | Kaiser et al. | 600/595 |
| 2013/0245436 A1 | 9/2013 | Tupin, Jr. et al. | |
| 2014/0039284 A1 | 2/2014 | Niwayama et al. | |
| 2014/0073486 A1 | 3/2014 | Ahmed et al. | |
| 2014/0074431 A1* | 3/2014 | Modi | G01C 22/006 702/160 |
| 2014/0099614 A1 | 4/2014 | Hu et al. | |
| 2014/0107493 A1 | 4/2014 | Yuen et al. | |
| 2014/0135612 A1 | 5/2014 | Yuen et al. | |
| 2014/0135631 A1 | 5/2014 | Brumback et al. | |
| 2014/0142403 A1 | 5/2014 | Brumback et al. | |
| 2014/0241626 A1* | 8/2014 | Sull et al. | 382/165 |
| 2014/0275821 A1 | 9/2014 | Beckman | |
| 2014/0275852 A1 | 9/2014 | Hong et al. | |
| 2014/0275854 A1 | 9/2014 | Venkatraman et al. | |
| 2014/0276119 A1 | 9/2014 | Venkatraman et al. | |
| 2014/0278139 A1 | 9/2014 | Hong et al. | |
| 2014/0288390 A1 | 9/2014 | Hong et al. | |
| 2014/0288391 A1 | 9/2014 | Hong et al. | |
| 2014/0288392 A1 | 9/2014 | Hong et al. | |
| 2014/0288435 A1 | 9/2014 | Richards et al. | |
| 2014/0288436 A1 | 9/2014 | Venkatraman et al. | |
| 2014/0288438 A1 | 9/2014 | Venkatraman et al. | |
| 2014/0378786 A1 | 12/2014 | Hong et al. | |
| 2014/0378787 A1 | 12/2014 | Brumback et al. | |
| 2014/0378844 A1 | 12/2014 | Fei | |
| 2014/0378872 A1 | 12/2014 | Hong et al. | |
| 2015/0025393 A1 | 1/2015 | Hong et al. | |
| 2015/0025394 A1 | 1/2015 | Hong et al. | |
| 2015/0196256 A1 | 7/2015 | Venkatraman et al. | |
| 2015/0201853 A1 | 7/2015 | Hong et al. | |
| 2015/0201854 A1 | 7/2015 | Hong et al. | |
| 2015/0223708 A1 | 8/2015 | Richards et al. | |
| 2015/0230743 A1 | 8/2015 | Silveira et al. | |
| 2015/0230761 A1 | 8/2015 | Brumback et al. | |
| 2015/0282713 A1 | 10/2015 | Fei | |
| 2015/0366469 A1 | 12/2015 | Harris et al. | |
| 2016/0034634 A9 | 2/2016 | Hong et al. | |
| 2016/0058312 A1 | 3/2016 | Han et al. | |
| 2016/0183818 A1 | 6/2016 | Richards et al. | |
| 2016/0302706 A1 | 10/2016 | Richards et al. | |
| 2016/0345881 A1 | 12/2016 | Sarantos et al. | |
| 2017/0027523 A1 | 2/2017 | Venkatraman et al. | |
| 2017/0164848 A1 | 6/2017 | Nadeau et al. | |

FOREIGN PATENT DOCUMENTS

| | | |
|---|---|---|
| CN | 101742981 A | 6/2010 |
| CN | 102008811 A | 4/2011 |
| CN | 202069586 U | 12/2011 |
| CN | 102389313 A | 3/2012 |
| CN | 102551686 A | 7/2012 |
| CN | 102750015 A | 10/2012 |
| CN | 102781310 A | 11/2012 |
| CN | 103093420 A | 5/2013 |
| EP | 1 297 784 A1 | 4/2003 |
| EP | 1 586 353 A1 | 10/2005 |
| EP | 1 721 237 | 8/2012 |
| WO | WO 2014/091424 A2 | 6/2014 |
| WO | WO 2014/091424 A3 | 6/2014 |

OTHER PUBLICATIONS

Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.

DesMarais, Christina (posted on Sep. 3, 2013) "Which New Activity Tracker is Best for You?" *Health and Home, Health & Fitness , Guides & Reviews*, [Retrieved on Sep. 23, 2013 at http://www.techlicious.com/guide/which-new-activity-tracker-is-right-for-you/] 4 pp.

Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.

U.S. Appl. No. 14/214,655, filed Mar. 14, 2014, Hong et al.

U.S. Appl. No. 14/250,256, filed Apr. 10, 2014, Hong et al.

Fitbit User's Manual, Last Updated Oct. 22, 2009, 15 pages.

Forerunner® 201 personal trainer owner's manual, (Feb. 2006) Garmin Ltd., 48 pp.

Forerunner® 301 personal trainer owner's manual, (Feb. 2006) Garmin Ltd., 66 pp.

Forerunner® 50 with ANT+Sport™ wireless technology, Owner's Manual, (Nov. 2007) Garmin Ltd., 44 pp.

Forerunner® 205/305 Owner's Manual, GPS-enabled trainer for runners, (2006-2008), Garmin Ltd., 80 pp.

Forerunner® 405CX Owner's Manual, "GPS-Enabled Sports Watch With Wireless Sync," (Mar. 2009), Garmin Ltd., 56 pp.

Forerunner® 110 Owner's Manual, (2010) "GPS-Enabled Sport Watch," Garmin Ltd., 16 pp.

Forerunner® 210 Owner's Manual, (2010) "GPS-Enabled Sport Watch," Garmin Ltd., 28 pp.

Forerunner® 410 Owner's Manual, (Jul. 2012) "GPS-Enabled Sport Watch With Wireless Sync," Garmin Ltd., 52 pp.

Forerunner® 10 Owner's Manual (Aug. 2012), Garmin Ltd., 10 pp.

Forerunner® 310XT Owner's Manual, Multisport GPS Training Device, (2009-2013), Garmin Ltd., 56 pp.

Forerunner® 405 Owner's Manual, (Mar. 2011) "GPS-Enabled Sport Watch With Wireless Sync," Garmin Ltd., 56 pp.

Forerunner® 910XT Owner's Manual, (Jan. 2013) Garmin Ltd., 56 pp.

Garmin Swim™ Owner's Manual (Jun. 2012), 12 pp.

Larklife, User Manual, (2012) *Lark Technologies*, 7 pp.

Lark/Larkpro, User Manual, (2012) "What's in the box," *Lark Technologies*, 7 pp.

Nike+ FuelBand GPS Manual, User's Guide (Product Release Date Unknown, downloaded Jul. 22, 2013), 26 pages.

(56) References Cited

OTHER PUBLICATIONS

Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N.D. User Manual, Polar® Listen to Your Body, *Manufactured by Polar Electro Oy*, 11 pages.
Rainmaker, (Jun. 25, 2012, updated Feb 16, 2013) "Garmin Swim watch In-Depth Review," [retrieved on Sep. 9, 2013 at http://www.dcrainmaker.com/2012/06/garmin-swim-in-depth-review.html, 38 pp.
Zijlstra, Wiebren, (2004) "Assessment of spatio-temporal parameters during unconstrained walking," Eur J Appl Physiol, 92:39-44.
U.S. Appl. No. 14/290,884, filed May 29, 2014, Richards et al.
U.S. Appl. No. 14/292,669, filed May 30, 2014, Hong et al.
U.S. Appl. No. 14/292,673, filed May 30, 2014, Venkatraman et al.
U.S. Appl. No. 14/295,059, filed Jun. 3, 2014, Venkatraman et al.
U.S. Appl. No. 14/295,076, filed Jun. 3, 2014, Venkatraman et al.
U.S. Appl. No. 14/295,122, filed Jun. 3, 2014, Venkatraman et al.
U.S. Appl. No. 14/295,144, filed Jun. 3, 2014, Hong et al.
U.S. Appl. No. 14/295,158, filed Jun. 3, 2014, Hong et al.
U.S. Appl. No. 14/295,161, filed Jun. 3, 2014, Hong et al.
U.S. Office Action, dated Aug. 4, 2014, issued in U.S. Appl. No. 13/924,784.
U.S. Office Action, dated Aug. 5, 2014, issued in U.S. Appl. No. 14/292,673.
U.S. Office Action, dated Jul. 31, 2014, issued in U.S. Appl. No. 14/295,122.
U.S. Office Action, dated Mar. 14, 2014, issued in U.S. Appl. No. 14/154,009.
U.S. Office Action, dated Aug. 22, 2014, issued in U.S. Appl. No. 14/250,256.
Cooper, Daniel (Aug. 16, 2013) Withings Pulse review, http://www.engadget.com/2013/08/16/withings-pulse-revew/, 8 pages.
LIFETRNR, User Manual (2003, specific date unknown), NB new balance®, Implus Footcare, LLC, 3 pages.
Rainmaker, (Jul. 25, 2013) "Basis B1 Watch In-Depth Review," [retrieved on Feb. 4, 2014 at http://www.dcrainmaker.com/2013/07/basis-b1-review.html], 56 pp.
"Withings pulse, Quick Installation Guide" (Jul. 24, 2013) Withings Pulse QIG, v 1.3, withings.com/pulse, 16 pages.
U.S. Appl. No. 14/599,039, filed Jan. 16, 2015, Venkatraman et al.
U.S. Notice of Allowance, dated Nov. 19, 2014, issued in U.S. Appl. No. 13/924,784.
U.S. Office Action, dated Oct. 22, 2014, issued in U.S. Appl. No. 14/290,884.
U.S. Notice of Allowance, dated Feb. 6, 2015, issued in U.S. Appl. No. 14/290,884.
U.S. Notice of Allowance, dated Sep. 23, 2014, issued in U.S. Appl. No. 14/292,669.
U.S. Notice of Allowance (Corrected Notice of Allowability), dated Oct. 14, 2014, issued in U.S. Appl. No. 14/292,669.
U.S. Notice of Allowance (Corrected Notice of Allowability), dated Dec. 31, 2014, issued in U.S. Appl. No. 14/292,669.
U.S. Notice of Allowance, dated Oct. 14, 2014, issued in U.S. Appl. No. 14/295,144.
U.S. Notice of Allowance, dated Dec. 3, 2014, issued in U.S. Appl. No. 14/295,144.
U.S. Notice of Allowance, dated Sep. 26, 2014, issued in U.S. Appl. No. 14/295,158.
U.S. Notice of Allowance (Corrected Notice of Allowability), dated Dec. 31, 2014, issued in U.S. Appl. No. 14/295,158.
U.S. Office Action, dated Jan. 23, 2015, issued in U.S. Appl. No. 14/507,184.
U.S. Office Action, dated Jan. 26, 2015, issued in U.S. Appl. No. 14/295,161.
U.S. Office Action, dated Jan. 27, 2015, issued in U.S. Appl. No. 14/507,173.
U.S. Notice of Allowance, dated Dec. 8, 2014, issued in U.S. Appl. No. 14/292,673.
U.S. Office Action, dated Sep. 18, 2014, issued in U.S. Appl. No. 14/295,059.
U.S. Notice of Allowance, dated Jan. 28, 2015, issued in U.S. Appl. No. 14/295,059.
U.S. Office Action, dated Dec. 24, 2014, issued in U.S. Appl. No. 14/295,076.
U.S. Notice of Allowance, dated Nov. 24, 2014, issued in U.S. Appl. No. 14/295,122.
U.S. Notice of Allowance (Corrected Notice of Allowability), dated Jan. 5, 2015, issued in U.S. Appl. No. 14/295,122.
U.S. Office Action, dated Sep. 29, 2014, issued in U.S. Appl. No. 14/154,009.
U.S. Notice of Allowance, dated Jan. 21, 2015, issued in U.S. Appl. No. 14/154,009.
U.S. Office Action, dated Nov. 25, 2014, issued in U.S. Appl. No. 14/154,019.
U.S. Office Action, dated Dec. 10, 2014, issued in U.S. Appl. No. 14/484,104.
U.S. Final Office Action, dated Nov. 21, 2014, issued in U.S. Appl. No. 14/250,256.
U.S. Office Action, dated Oct. 7, 2014, issued in U.S. Appl. No. 14/481,762.
U.S. Final Office Action, dated Dec. 19, 2014, issued in U.S. Appl. No. 14/481,762.
U.S. Office Action, dated Jun. 22, 2015, issued in U.S. Appl. No. 14/693,710.
U.S. Notice of Allowance, dated Jul. 27, 2015, issued in U.S. Appl. No. 14/693,710.
U.S. Final Office Action, dated May 11, 2015, issued in U.S. Appl. No. 14/507,184.
U.S. Notice of Allowance, dated Aug. 11, 2015, issued in U.S. Appl. No. 14/507,184.
U.S. Notice of Allowance, dated Apr. 14, 2015, issued in U.S. Appl. No. 14/295,161.
U.S. Notice of Allowance, dated Jul. 28, 2015, issued in U.S. Appl. No. 14/295,161.
U.S. Office Action, dated May 11, 2015, issued in U.S. Appl. No. 14/673,630.
U.S. Notice of Allowance, dated Apr. 17, 2015, issued in U.S. Appl. No. 14/507,173.
U.S. Notice of Allowance (Corrected Notice of Allowability), dated Jul. 16, 2015, issued in U.S. Appl. No. 14/507,173.
U.S. Office Action, dated Jun. 8, 2015, issued in U.S. Appl. No. 14/673,634.
U.S. Notice of Allowance (Corrected Notice of Allowability), dated Mar. 5, 2015, issued in U.S. Appl. No. 14/292,673.
U.S. Notice of Allowance (Corrected Notice of Allowability), dated Mar. 11, 2015, issued in U.S. Appl. No. 14/295,059.
U.S. Final Office Action, dated Apr. 15, 2015, issued in U.S. Appl. No. 14/295,076.
U.S. Notice of Allowance, dated Mar. 20, 2015, issued in U.S. Appl. No. 14/154,019.
U.S. Notice of Allowance (Corrected Notice of Allowability), dated May 14, 2015, issued in U.S. Appl. No. 14/154,019.
U.S. Notice of Allowance, dated Mar. 19, 2015, issued in U.S. Appl. No. 14/484,104.
U.S. Notice of Allowance (Corrected Notice of Allowability), dated May 6, 2015, issued in U.S. Appl. No. 14/484,104.
U.S. Office Action, dated Mar. 12, 2015, issued in U.S. Appl. No. 14/481,020.
U.S. Final Office Action, dated Jul. 7, 2015, issued in U.S. Appl. No. 14/481,020.
U.S. Office Action, dated Jul. 8, 2015, issued in U.S. Appl. No. 14/250,256.
U.S. Office Action, dated Jul. 7, 2015, issued in U.S. Appl. No. 14/481,762.
Chinese First Office Action (no translation) dated Aug. 7, 2015 issued in CN 201410243180.6.

(56) References Cited

OTHER PUBLICATIONS

U.S. Notice of Allowance (Corrected Notice of Allowability), dated Dec. 18, 2015, issued in U.S. Appl. No. 14/507,184.
U.S. Notice of Allowance, dated Nov. 25, 2015, issued in U.S. Appl. No. 14/673,630.
U.S. Final Office Action, dated Nov. 4, 2015, issued in U.S. Appl. No. 14/673,634.
U.S. Office Action, dated Oct. 22, 2015, issued in U.S. Appl. No. 14/295,076.
U.S. Office Action, dated Oct. 27, 2015, issued in U.S. Appl. No. 14/481,020.
U.S. Final Office Action, dated Oct. 23, 2015, issued in U.S. Appl. No. 14/250,256.
U.S. Final Office Action, dated Nov. 5, 2015, issued in U.S. Appl. No. 14/481,762.
U.S. Office Action, dated Nov. 19, 2015, issued in U.S. Appl. No. 14/724,750.
Dunn et al. (2007) "A Novel Ring Shaped Photodiode for Reflectance Pulse Oximetry in Wireless Applications," IEEE Sensors Conference, pp. 596-599.
U.S. Appl. No. 14/724,750, filed May 28, 2015, Sarantos et al.
U.S. Appl. No. 14/954,753, filed Nov. 30, 2015, Richards et al.
Litigation Document—"Compliant for Patent Infringement," filed Oct. 29, 2015, in U.S. District Court of Delaware (Court Docket No. 1:15-cv-00990-RGA) [Re: U.S. Pat. Nos. 8,868,377, 8,920,332, and 9,089,760].
Litigation Document—"Report on the Filing or Determination of an Action Regarding a Patent or Trademark," filed Oct. 29, 2015, in U.S. District Court of Delaware (Court Docket No. 1:15-cv-00990-RGA) [Re: U.S. Pat. Nos. 8,868,377, 8,920,332, and 9,089,760].
U.S. Notice of Allowance, dated Apr. 15, 2016, issued in U.S. Appl. No. 14/954,753.
U.S. Notice of Allowance (Corrected Notice of Allowability), dated Mar. 21, 2016, issued in U.S. Appl. No. 14/673,630.
U.S. Office Action, dated Mar. 17, 2016, issued in U.S. Appl. No. 14/250,256.
U.S. Notice of Allowance, dated Mar. 8, 2016, issued in U.S. Appl. No. 14/724,750.
Chinese First Office Action dated Aug. 7, 2015 issued in CN 201410243180.6.
U.S. Office Action, dated Oct. 26, 2016, issued in U.S. Appl. No. 15/195,911.
U.S. Final Office Action, dated Oct. 19, 2016, issued in U.S. Appl. No. 14/481,762.
U.S. Office Action dated Sep. 8, 2016, issued in U.S. Appl. No. 15/192,447.
Chinese First Office Action dated Aug. 3, 2016 issued in Application No. CN 201410243169.X.
Litigation Document—"Respondents' Opposition to Complainant's Petition for Review of the Initial Determination Granting Summary Determination that the Asserted Patents are Directed to Ineligible Subject Matter under 35 U.S.C. § 101," filed Aug. 8, 2016, in United States International Trade Commission, Washington, D.C. (Investigation No. 337-TA-973) (4446833v1/014972) [In the Matter of Certain Wearable Activity Tracking Devices, Systems, and Components Thereof].
Litigation Document—"Complainant's Petition for Review of the Initial Determination Granting Summary Determination that the Asserted Patents are Directed to Ineligible Subject Matter under 35 U.S.C. § 101," filed Aug. 1, 2016, in United States International Trade Commission, Washington, D.C. (Investigation No. 337-TA-973) [In the Matter of Certain Wearable Activity Tracking Devices, Systems, and Components Thereof].
U.S. Appl. No. 15/246,387, filed Aug. 24, 2016, Venkatraman et al.
Litigation Document—"Summary Pursuant to 19 C.F.R. § 210.43(b)(2) of Complainant's Petition for Review of the Initial Determination Granting Summary Determination that the Asserted Patents are Directed to Ineligible Subject Matter under 35 U.S.C. § 101," filed Aug. 1, 2016, in United States International Trade Commission, Washington, D.C. (Investigation No. 337-TA-973) [In the Matter of Certain Wearable Activity Tracking Devices, Systems, and Components Thereof].
Litigation Document—"Notice of Commission Determination to Review an Initial Determination Granting Respondents' Motion for Summary Determination that Certain Asserted Claims are Directed to Ineligible Subject Matter under 35 U.S.C. § 101; and on Review to Remand the Investigation to the Presiding Administrative Law Judge," issued Sep. 7, 2016, in United States International Trade Commission, Washington, D.C. (Investigation No. 337-TA-973) [In the Matter of Certain Wearable Activity Tracking Devices, Systems, and Components Thereof].
U.S. Notice of Allowance, dated Jan. 23, 2017, issued in U.S. Appl. No. 15/195,911.
U.S. Office Action, dated Jul. 13, 2016, issued in U.S. Appl. No. 14/673,634.
U.S. Office Action, dated Feb. 9, 2017, issued in U.S. Appl. No. 14/673,634.
U.S. Notice of Allowance, dated May 24, 2016, issued in U.S. Appl. No. 14/295,076.
U.S. Office Action dated Dec. 22, 2016, issued in U.S. Appl. No. 14/599,039.
U.S. Final Office Action, dated May 13, 2016, issued in U.S. Appl. No. 14/481,020.
U.S. Examiner's Answer to Appeal Brief, dated Jan. 23, 2017, issued in U.S. Appl. No. 14/481,020.
U.S. Final Office Action, dated Jun. 29, 2016, issued in U.S. Appl. No. 14/250,256.
U.S. Office Action, dated Jan. 9, 2017, issued in U.S. Appl. No. 14/250,256.
U.S. Office Action, dated May 11, 2016, issued in U.S. Appl. No. 14/481,762.
U.S. Office Action, dated Apr. 12, 2017, issued in U.S. Appl. No. 14/481,762.
U.S. Final Office Action dated Feb. 7, 2017, issued in U.S. Appl. No. 15/192,447.
Chinese First Office Action dated Sep. 27, 2016 issued in Application No. CN 201410018701.8.
Chinese First Office Action dated Sep. 2, 2016 issued in Application No. CN 201510745382.5.
Chinese Second Office Action [No translation] dated Mar. 22, 2017 issued in Application No. CN 201510745382.5.
Chinese Second Office Action [No translation] dated Mar. 27, 2017 issued in Application No. CN 201410243169.X.
Chinese First Office Action dated Sep. 26, 2016 issued in Application No. CN 201410243178.9.
Chinese First Office Action [No translation] dated Mar. 3, 2017 issued in Application No. CN 201610622453.7.
European Extended Search Report dated Oct. 25, 2016 issued in Application No. EP 16 16 8661.3.
Litigation Document—"Complaint for Patent Infringement," filed Sep. 3, 2015, in U.S. District Court of Delaware (Court Docket No. 1: 15-cv-00775-RGA).
Litigation Document—"Report on the Filing or Determination of an Action Regarding a Patent or Trademark," filed Sep. 3, 2015, in U.S. District Court of Delaware (Court Docket No. 1: 15-cv-00775-RGA).
Litigation Document—"Order No. 24: Initial Determination Granting Respondents' Motion for Summary Determination of Invalidity under 35 U.S.C. § 101 with respect to all Three Asserted Patents and Terminating the Investigation in its Entirety," filed Jul. 19, 2016, in United States International Trade Commission, Washington, D.C. (Investigation No. 337-TA-973) [In the Matter of Certain Wearable Activity Tracking Devices, Systems, and Components Thereof].
Litigation Document—"Declaration of Majid Sarrafzadeh in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [In the Matter of Certain Wearable Activity Tracking Devices, Systems, and Components Thereof] [Exhibit 7].

(56) References Cited

OTHER PUBLICATIONS

Litigation Document—"Kiaei Declaration in Support of Complainant's Supplemental Brief Regarding Construction of "Operating the Heart Rate Monitor in a Worn Detection Mode" under 35 U.S.C. § 112(f)," filed Apr. 29, 2016, in United States International Trade Commission, Washington, D.C. (Investigation No. 37-TA-973) [In the Matter of Certain Wearable Activity Tracking Devices, Systems, and Components Thereof] [Exhibit 8].
Litigation Document—"Memorandum in Support of Respondents' Motion for Summary Determination that the Asserted Patents are Directed to Ineligible Subject Matter under 35 U.S.C. § 101," filed May 23, 2016, in United States International Trade Commission, Washington, D.C. (Investigation No. 337-TA-973) (44325007v1/014972) [In the Matter of Certain Wearable Activity Tracking Devices, Systems, and Components Thereof].
Litigation Document—"Grimes Declaration in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [In the Matter of Certain Wearable Activity Tracking Devices, Systems, and Components Thereof] [Exhibit 28].
Litigation Document— "Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 337-TA-973) [In the Matter of Certain Wearable Activity Tracking Devices, Systems, and Components Thereof].
U.S. Appl. No. 61/736,310, filed Dec. 12, 2012, William Ahmed et al., entitled "Fitness Monitoring Systems and Methods Based on Continuous Collection of Physiological Data," 61pp [Exhibit 4].
U.S. Appl. No. 61/696,525, filed Sep. 4, 2012, William Ahmed et al., entitled "Fitness Monitoring Systems and Methods Based on Continuous Collection of Physiological Data," 47pp [Exhibit 5].
Gasparrini et al. (2013) "Evaluation and Possible Improvements of the ANT Protocol for Home Heart Monitoring Applications," *IEEE*, 978-1-4673-2874-6/13, 7pp [Exhibit 6].
"UP3™, The world's most advanced tracker," (Oct. 14, 2015) *Jawbone*, 10pp [Exhibit 12].
"UP4™, A fitness tracker so advanced it pays," (Oct. 14, 2015) *Jawbone*, 12pp [Exhibit 13].
"User's Guide, Mio Drive+ Petite," User's guide and how-to videos available at www.mioglobal.com, 3pp [Exhibit 16].

"Solo 915, Heart Rate + Calorie Monitor," (2009) *Sportline®*, [retrieved on Oct. 15, 2010 at www.sportline.com] 25pp [Exhibit 17].
U.S. Notice of Allowance dated Oct. 14, 2014 issued in U.S. Appl. No. 14/295,144, 5pp [Exhibit 18].
"Health Touch™ Plus User Guide," (2011) *Timex Group USA, Inc.*, 12pp [Exhibit 18].
Czarnul, Pawel (Jun. 6-8, 2013) "Design of a Distributed System using Mobile Devices and Workflow Management for Measurement and Control of a Smart Home and Health," Sopot, Poland, *IEEE*, pp. 184-192, 10pp [Exhibit 19].
Rabinovich, Roberto A., and Louvaris, Zafeiris et al. (Feb. 8, 2013) "Validity of Physical Activity Monitors During Daily Life in Patients With COPD," *ERJ Express, European Respiratory Society*, 28pp [Exhibit 24].
Horvath et al. (2007) "The effect of pedometer position and normal gait asymmetry on step count accuracy," *Appl. Physiol. Nutr. Metab.*, 32:409-415, 8pp [Exhibit 32].
Graser et al. (2007) "Effects of Placement, Attachment, and Weight Classification on Pedometer Accuracy," *Journal of Physical Activity and Health*, 4(4):359-369, 13pp [Exhibit 33].
Vyas et al. (2012) "Machine Learning and Sensor Fusion for Estimating Continuous Energy Expenditure," *AI Magazine*, pp. 55-61, 13pp [Exhibit 42].
"New Lifestyles, NL-800 Activity Monitor, User's guide & record book," (2005), New Lifestyles, Inc., 37pp.
"StepWatch Step Activity Monitor, U.S. Pat. No. 5,485,402," (2001) StepWatch™, *Prosthetics Research Study*, 7pp.
U.S. Office Action dated Mar. 15, 2017, issued in U.S. Appl. No. 15/370,303.
U.S. Notice of Allowance dated May 24, 2017, issued in U.S. Appl. No. 15/192,447.
Chinese Second Office Action dated Mar. 22, 2017 issued in Application No. CN 201510745382.5.
Chinese Second Office Action dated Mar. 27, 2017 issued in Application No. CN 201410243169.X.
Chinese First Office Action dated Mar. 3, 2017 issued in Application No. CN 201610622453.7.
Litigation Document—"Plaintiffs Original Complaint for Patent Infringement," filed Jan. 4, 2016, in U.S. District Court for the Eastern District of North Carolina (Court Docket No. 5:16-cv-00002-FL) [Re: U.S. Pat. Nos. 8,923,941, 8,886,269, 8,929,965 and 8,989,830], 11 pages.
U.S. Appl. No. 15/494,257, filed Apr. 21, 2017, Richards et al.
US Patent Trial and Appeal Board's Decision on Appeal, dated Oct. 9, 2018, issued in U.S. Appl. No. 14/250,256.
US Patent Trial and Appeal Board's Decision on Appeal, dated Sep. 14, 2018, issued in U.S. Appl. No. 14/481,020.

\* cited by examiner

MULTIMODE SENSOR DEVICES

CROSS REFERENCE TO RELATED APPLICATIONS

This application claims the benefit under 35U.S.C. 517 119(e)(1) of U.S. Provisional Patent Application No. 61/800, 095, filed Mar. 15, 2013, which is hereby incorporated by reference in its entirety; this application also claims priority as a continuation-in-part under 35U.S.C. 517 120to U.S. patent application Ser. No. 13/156,304, filed on Jun. 8, 2011, which claims the benefit under 35U.S.C. 517 119(e) to U.S. Provisional Application No. 61/388,595, filed on Sep. 30, 2010and provisional application No. 61/390,811filed on Oct. 7, 2010.

BACKGROUND

Sensor devices can infer biometrics of interest from sensor data that are associated with activities of a user. In many implementations of sensor devices, however, the high accuracy of biometric estimates is achieved by limiting activity types and/or activity intensities that the sensor devices can monitor. For example, pedometers are recommended to be worn on the left mid-axillary position for the most accurate step counts (Horvath et al. 2007). Even with the ideal placement location, pedometers can fail to provide reliable step counts, either by overcounting or undercounting steps in some activities such as bus riding.

The placement of sensor devices is a significant constraint. Users of sensor devices prefer to wear their portable sensor devices in convenient locations. However, these convenient locations are often not ideal for collecting biometric data. For example, the location of the sensor device may be remote from the body part or body parts that are mainly involved in the activity or have the strongest biometric signal. For this reason, current sensor devices sacrifice convenience for accuracy or vice versa.

Recent advances in sensor, electronics, and power source miniaturization have allowed the size of personal health monitoring devices, also referred to herein as "biometric tracking" or "biometric monitoring" devices, to be offered in small sizes. These biometric monitoring devices may collect, derive, and/or provide one or more of the following types of information: step counts, ambulatory speed, distance traveled cadence, heart rate, calorie burn, floors climbed and/or descended, location and/or heading, elevation, etc. However, the miniature size of the product limits the electric power it supplies. Therefore, there is the need for energy saving methods and hardware that allow high speed and accurate computation of biometric information.

The inventions disclosed herein enable sensor devices to use one or more modes to achieve computation speed and accuracy while maintaining energy efficiency.

SUMMARY

This disclosure enables sensor devices to use one or more modes. In some embodiments, different types of modes are run simultaneously. In other embodiments, the most appropriate mode or set of modes is selected to be used at any one moment in time. These modes include, but are not limited to different motion intensities, sensor device placement locations (e.g. where it is worn) and/or activity types. Automatically or manually switching between the modes, the sensor devices track biometric data more accurately regardless of the motion intensity, placement location, and/or activity type, while maintaining computation efficiency.

The disclosure provides BMDs that have multiple device modes depending on operational conditions of the devices, e.g., motion intensity, device placement, and/or activity type, the device modes are associated with various data processing algorithms. In some embodiments, methods for tracking physiological metrics using the BMDs are provided. In some embodiments, the process and the BMD applies a time domain analysis on data provided by a sensor of the BMD when the data has a high signal (e.g., high signal-to-noise ratio), and applies a frequency domain analysis on the data when the data has a low signal, which contributes to improved accuracy and speed of biometric data.

Some embodiments of the disclosure provide a method of tracking a user's physiological activity using a worn biometric monitoring device (BMD). The BMD has one or more sensors providing output data indicative of the user's physiological activity. The method involves analyzing sensor output data provided by the biometric monitoring device to determine that the output data has a relatively low signal-to-noise ratio (SNR) while the user is active. Upon the determination, the BMD collects the sensor output data for a duration sufficient to identify a periodic component of the data. Then the BMD uses frequency domain analysis of the collected sensor output data to process and/or identify said periodic component. The BMD determines a metric of the user's physiological activity from the periodic component of the collected sensor output data. Finally, the BMD may present the metric of the user's physiological activity. In some embodiments, the one or more sensors of the BMD include a motion sensor, and the output data includes motion intensity from the motion sensor. In some embodiments, the worn biometric monitoring device includes a wrist-worn or arm-worn device.

Some embodiments of the disclosure provide a method of tracking a user's physiological activity using a worn biometric monitoring device (BMD). The method includes the following operations: (a) analyzing sensor output data provided by the biometric monitoring device to determine that the user is engaged in a first activity that produces a relatively high SNR in the sensor output data; (b) quantifying a physiological metric by analyzing a first set of sensor output data in the time domain; (c) analyzing subsequent sensor output data provided by the biometric monitoring device to determine that the user is engaged in a second activity that produces a relatively low SNR in the subsequent sensor output data; and (d) quantifying the physiological metric from a periodic component of a second set of sensor output data by processing the second set of sensor output data using a frequency domain analysis. For instance, the first activity may be running with hands moving freely. The second activity may be walking when pushing a stroller. In some embodiments, the frequency domain analysis includes one or more of the following: Fourier transform, cepstral transform, wavelet transform, filterbank analysis, power spectral density analysis and/or periodogram analysis.

In some embodiments, the quantifying operation in (d) requires more computation per unit of the sensor output data duration than the quantifying in (b). In some embodiments, the quantifying in (d) requires more computation per unit of the physiological metric than the quantifying in (b).

In some embodiments, (b) and (d) each involves: identifying a periodic component from the sensor output data;

determining the physiological metric from the periodic component of the sensor output data; and presenting the physiological metric.

In some embodiments, the sensor output data include raw data directly obtained from the sensor without preprocessing. In some embodiments, the sensor output data include data derived from the raw data after preprocessing.

In some embodiments, the worn biometric monitoring device is a wrist-worn or arm-worn device.

In some embodiments, the operation of analyzing sensor output data in (a) or (c) involves characterizing the output data based on the signal norms, signal energy/power in certain frequency bands, wavelet scale parameters, and/or a number of samples exceeding one or more thresholds.

In some embodiments, the process further involves analyzing biometric information previously stored on the biometric monitoring device to determine that the user is engaged in the first or the second activity.

In some embodiments, the one or more sensors include a motion sensor, wherein analyzing sensor output data in (a) or (c) involves using motion signal to determine whether the user is engaged in the first activity or the second activity. In some embodiments, the first activity involves free motion of a limb wearing the biometric monitoring device during activity. In some embodiments, the second activity comprises reduced motion of the limb wearing the biometric monitoring device during activity. In some embodiments, the second activity involves the user holding a substantially non-accelerating object with a limb wearing the biometric monitoring device.

In some embodiments, analyzing the first set of sensor output data in the time domain involves applying peak detection to the first set of sensor output data. In some embodiments, analyzing the second set of sensor output data involves identifying a periodic component of the second set of sensor output data. In some embodiments, the first set of sensor output data includes data from only one axis of a multi-axis motion sensor, wherein the second set of sensor output data include data from two or more axis of the multi-axis motion sensor.

In some embodiments, the frequency domain analysis involves frequency band passing time domain signal, and then applying a peak detection in the time domain. In some embodiments, the frequency domain analysis includes finding any spectral peak/peaks that is/are a function of the average step rate. In some embodiments, the frequency domain analysis involves performing a Fisher's periodicity test. In some embodiments, the frequency domain analysis includes using a harmonic to estimate period and/or test periodicity. In some embodiments, the frequency domain analysis include performing a generalized likelihood ratio test whose parametric models incorporate harmonicity of motion signal.

Some embodiments further involve analyzing sensor output data to classify motion signals into two categories: signals generated from steps and signals generated from activities other than steps.

In some embodiments, the physiological metric provided by the BMD includes a step count. In some embodiments, the physiological metric includes a heart rate. In some embodiments, the physiological metric includes number of stairs climbed, calories burnt, and/or sleep quality.

Some embodiments further involves applying a classifier to the sensor output data and the subsequent sensor output data to determine the placement of the biometric monitoring device on the user. In some embodiments, the processing in (b) comprises using information regarding the placement of the biometric monitoring device to determine the value of the physiological metric.

Some embodiments further include applying a classifier to the sensor output data and the subsequent sensor output data to determine whether the user is engaged in the first activity and/or the second activity. In some embodiments, the first activity is one of the following: running, walking, elliptical machine, stair master, cardio exercise machines, weight training, driving, swimming, biking, stair climbing, and rock climbing. In some embodiments, the processing in (b) includes using information regarding activity type to determine the value of the physiological metric.

Some embodiments provide a method of tracking a user's physiological activity using a worn BMD, the method involves: (a) determining that the user is engaged in a first type of activity by detecting a first signature signal in sensor output data, the first signature signal being selectively associated with the first type of activity; (b) quantifying a first physiological metric for the first type of activity from a first set of sensor output data; (c) determining that the user is engaged in a second type of activity by detecting a second signature signal in sensor output data, the second signature signal being selectively associated with the second type of activity and different from the first signature signal; and (d) quantifying a second physiological metric for the second type of activity from a second set of sensor output data. In some embodiments, the first signature signal and the second signature signal include motion data. In some embodiments, the first signature signal and the second signature signal further include one or more of the following: location data, pressure data, light intensity data, and/or altitude data.

Some embodiments provide a BMD that includes one or more sensors providing sensor output data comprising information about a user's activity level when the biometric monitoring device is worn by the user. The BMD also includes control logic configured to: (a) analyze sensor output data to characterize the output data as indicative of a first activity associated with a relatively high signal level or indicative of a second activity associated with a relatively low signal level; (b) process the sensor output data indicative of the first activity to produce a value of a physiological metric; and (c) process the sensor output data indicative of the second activity to produce a value of the physiological metric. In some embodiments, the processing of (b) requires more computation per unit of the physiological metric than the processing of (c).

Some embodiments provide a BMD having control logic that is configured to: (a) analyzing sensor output data provided by the biometric monitoring device to determine that the user is engaged in a first activity that produces a relatively high SNR in the sensor output data; (b) quantifying a physiological metric by analyzing the sensor output data in the time domain; (c) analyzing subsequent sensor output data provided by the biometric monitoring device to determine that the user is engaged in a second activity that produces a relatively low SNR in the subsequent sensor output data; and (d) quantifying the physiological metric from a periodic component of the subsequent sensor output data by processing the subsequent sensor output data using a frequency domain analysis. In some embodiments, the analyzing in (d) requires more computation per unit of the physiological metric than the analyzing in (b).

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals may refer to similar elements.

DETAILED DESCRIPTION

Introduction

Figure 1:
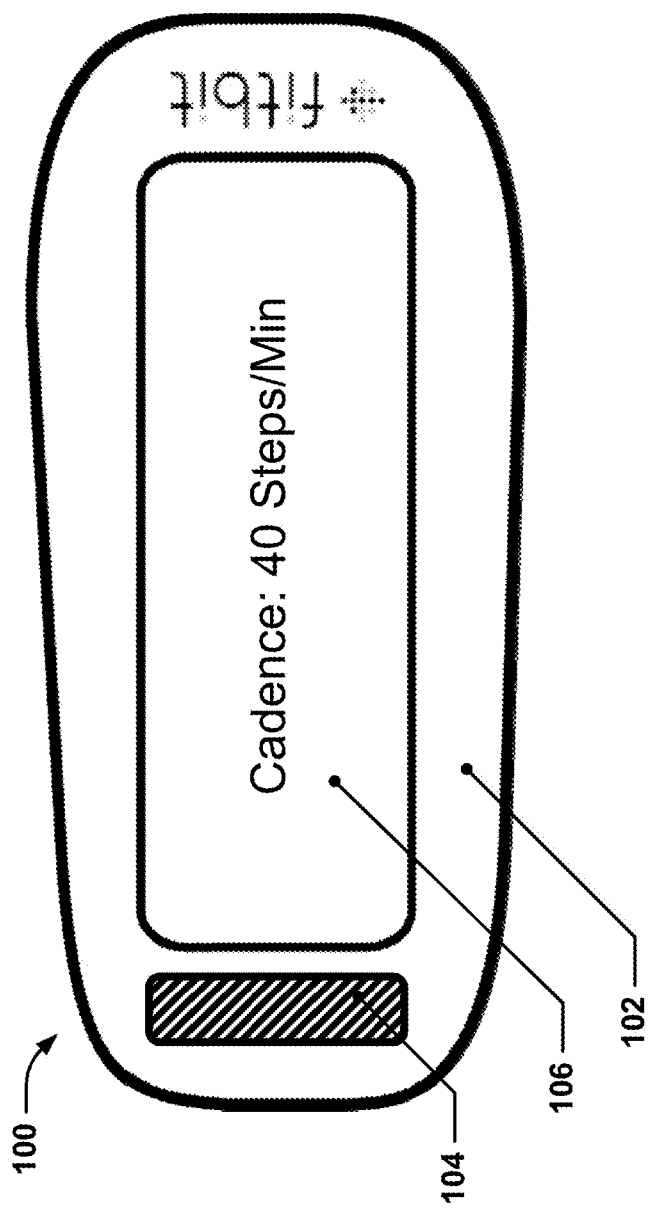
FIG. 1 shows an example of a portable biometric monitoring device having a button and a display according to some embodiments of the disclosure.

Sensor devices or Biometric Monitoring Devices (BMDs) according to embodiments described herein typically have shapes and sizes that are suitable for being coupled to (e.g., secured to, worn, borne by, etc.) the body or clothing of a user. BMDs are also referred to as biometric tracking devices herein. The devices collect one or more types of physiological and/or environmental data from embedded sensors and/or external devices.

In many applications, users of BMDs prefer to wear the BMD on their wrists. Therefore, in some embodiments, BMDs are implemented as watch-like, wrist-worn devices. Although many activity signatures are present in data obtained from the wrist or the arm, the data get inherently corrupted by unwanted motion and ambient noise. This leads to challenges in trying to infer certain user activities such as steps by using data obtained from the sensor device worn on the wrist. This disclosure provides solution to this problem by providing multiple modes to ease the inference problem.

Some embodiments use automated methods to determine the modes. Some embodiments use user inputs to determine the modes. Various embodiments provide different data processing algorithms suitable for different user activities and conditions.

BMDs are typically quite small due to practical considerations. People who wish to monitor their performance are unlikely to want to wear a large, bulky device that may interfere with their activities or that may look unsightly. As a result, biometric monitoring devices are often provided in small form factors to allow for light weight and ease of carrying. Such small form factors often necessitate some design compromises. For example, there may be limited space for displays, controls, and other components of the biometric monitoring device within the device housing. One system component that may be limited in size or performance is the power source, e.g., a battery, capacitor, etc., of the biometric monitoring device. In many implementations, the biometric monitoring device may be in an "always on" state to allow it to continually collect biometric data throughout the day and night. Given that the sensors and processor(s) of the biometric monitoring device must generally remain powered to some degree in order to collect the biometric data, it may be advantageous to implement power-saving features elsewhere in the device, e.g., such as by causing the display to automatically turn off after a period of time, or by measuring certain data such as heart rate data momentarily on demand indicated by a user-gesture. A typical user gesture may be provided by pressing a button on the biometric monitoring device, flipping the biometric monitoring device over and back, or double-tapping the housing of the biometric monitoring device, touching a surface area, or placing a body part near a proximity sensor.

There is generally a trade-off between speed and accuracy of biometric data for biometric data such as step counts, cadence, and heart rate. This trade-off is further exacerbated by the limited power supply of a miniaturized BMD. This disclosure address this problem by providing BMDs that have multiple device modes depending on operational conditions of the devices, e.g., motion intensity, device placement, and/or activity type.

In some embodiments, a mode may be employed alone. In other embodiments, multiple modes may be combined at a particular instant. For example, when a user is wearing a BMD on her dominant hand, swinging her hands freely, and walking up a flight of stairs, the device may simultaneously employ a free motion mode (motion intensity), a stairclimbing mode (activity type), and a dominant hand mode (device placement). In some embodiments, one or more of the modes may be selected by automatic triggers as further described below. In some embodiments, one or more of the modes may be manually selected by the user through a user interface.

In some embodiments, data collected by a sensor device is communicated or relayed to other devices. For example, while the user is wearing a sensor device, the sensor device may calculate and store the user's step count using one or more sensors. The device then transmits data representative of the user's step count to an account on a web service such as computer, mobile phone, or health station where the data may be stored, processed, and visualized by the user. Indeed, the sensor device may measure or calculate a plurality of other physiological metrics in addition to, or in place of, the user's step count. These include, but are not limited to, energy expenditure (e.g., calorie burned), floors climbed and/or descended, heart rate, heart rate variability, heart rate recovery, location and/or heading (e.g., through GPS), elevation, ambulatory speed and/or distance traveled, swimming lap count, swimming stroke type, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate.

In some embodiments, the sensor device may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field.

Furthermore, the sensor device may calculate metrics derived from the combination of the aforementioned data. For example, the sensor device may calculate the user's stress and/or relaxation levels through a combination of heart rate variability, skin conduction, noise pollution, and sleep quality. In another example, the sensor device may determine the efficacy of a medical intervention (e.g., medication) through the combination of medication intake, sleep and/or activity data. In yet another example, the sensor device may determine the efficacy of an allergy medication through the combination of pollen data, medication intake, sleep and/or activity data.

While the examples presented above illustrate the calculation of metrics on a sensor device, they may be performed in part or wholly on an external system (e.g. web server, mobile phone, personal computer). Indeed, these examples are provided for illustration only and are not intended to be limiting or exhaustive. Further embodiments and implementations of sensor devices can be found in U.S. patent application Ser. No. 13/156,304, titled "Portable Biometric Monitoring Devices and Methods of Operating Same" filed Jun. 8, 2011 which is entirely incorporated herein by reference.

Sensors are the tracking device's basic sensing hardware, e.g., accelerometers, magnetometers, gyroscopes, PPG sensors, etc. Details of various sensors and data types are further described hereinafter.

Sensor output data is a direct output from the tracking device's sensors. Examples include acceleration, light intensity, etc. This data varies with time and may contain constant or variable frequency and/or amplitude components. It may contain biometric information about the user's activity and/or environmental information about ambient conditions that exist independently of the user's activity.

In some embodiments, sensor output data include raw data directly obtained from the sensor without preprocessing. In some embodiments, sensor output data include data derived from the raw data after preprocessing.

Physiological metric is a physiologically relevant metric determined from the tracking device's sensor output data. It is sometimes referred to as a biometric performance metric. Physiological metrics may be characterized in various ways. For instance, it may be characterized by (1) basic units of physiological activity, e.g., steps, swimming stokes, pedal strokes, heartbeats, etc.; (2) increments of physiological output, e.g., pool laps, flights of stairs, heart rate, etc.; or (3) goals, including default or customized goals, e.g., 10,000 steps in a day.

"Activity type mode" as used herein refers to a device mode associated with a distinct user activity such as walking/running, rock climbing, sleeping, bicycling, swimming, etc. Each activity type mode may have an associated trigger and sensor data processing algorithm.

"Trigger" is used with reference to event(s) that cause the tracking device to enter a particular device mode.

Some device operations may be unique to particular activity type modes. Examples include displayed content, display screen sequences, etc.

A "sensor data processing algorithm" is used in reference to a computational process associated with a device mode. The sensor data processing algorithm is used to convert sensor output data to a physiological measure defined for the activity type. A tracking device will have multiple sensor data processing algorithms, each associated with one or more activity type modes. In some embodiments, different motion intensity modes have different sensor data processing algorithms.

Various motion intensity modes may be combined with an activity type mode. Motion intensity modes include two or more modes. In some embodiments, motion intensity modes have a high, an intermediate, and a low intensity mode. Each motion intensity mode having its own trigger and/or sensor data processing algorithm, and possibly other feature such as display content. In one example, a motion intensity mode distinguishes high activity (e.g., walking) vs. low activity (e.g., running). Another example distinguishes between walking with arms freely swinging and walking with arms fixed to a stationary object such as a treadmill handle. Typically, the tracking device will determine the same physiological metric for different motion intensity modes of the same activity type, so the device may determine a step count for both walking with arms freely swinging and walking with arms fixed.

Motion intensity modes are often deployed to address a device's current environment or context. For example, the data processing algorithm for a motion intensity mode may be designed to improve the accuracy of the information output for a particular environment or context, and/or save power in such environment or context. Some data processing algorithms require more processing power and hence consume more energy, and such algorithms should be used only when needed for accuracy. As an example, activity sub-type modes producing periodic signals with large amplitudes or signal-to-noise ratios (SNRs) may be processed inexpensively in the time domain, while other sub-type modes producing low amplitudes or signal-to-noise ratios may need to be processed with a computationally demanding algorithm in the frequency domain.

The term "monitor" is used with reference to a tracking device mode that presents monitored information about a distinct physiological activity such as heartbeats or steps. A monitor as a device mode is different from an activity type mode as seen in a classic example of a heart rate monitor, which is not specific to an activity type. A heart rate monitor may measure and/or present the basic unit of cardiac activity (heartbeat) and/or increments of cardiac activity (heart rate). A tracking device may have multiple monitors, each with its own trigger and sensor data processing algorithm. Other device operations that may be specific to monitors include displayed content, display screen sequences, etc. A monitor may have sub-modes with their own triggers and data processing algorithms as discussed for activity type modes.

Device state mode is used with reference to operational modes associated with various states of the hardware. Examples include a high/low battery mode, a syncing mode, timer mode, stopwatch mode, annotation mode, etc.

FIG. 1 shows a Biometric monitoring device (BMD) that may implement the multimode functions disclosed herein.

The BMD 100 in FIG. 1 includes a housing 102 that contains the electronics associated with the biometric monitoring devices 100. Among other sensors, the housing 102 includes a motion sensor. The BMD also has a button 104 to receive user input through button presses. Under certain context, one kind of button press received through button 104 may represent manual command to change the mode of the BMD in manners described below. The BMD 100 also includes a display 106 that may be accessible/visible through the housing 102. The components that may be integrated in a BMD is further illustrated in a schematic diagram shown in FIG. 7 below.

Figure 2:
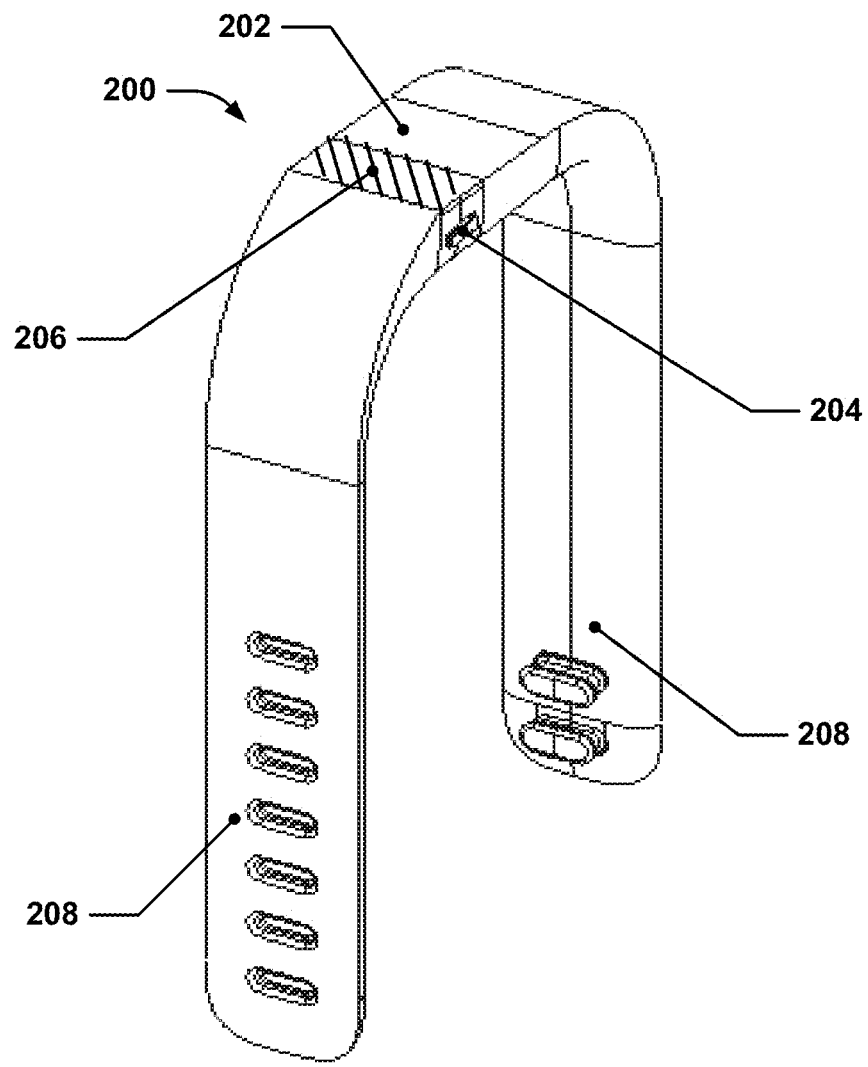
FIG. 2 shows an example of a wrist-watch like biometric monitoring device according to some embodiments of the disclosure.

FIG. 2 depicts another embodiment of a BMD having multimode functions that may be worn on a person's forearm like a wristwatch, much like a Fitbit FLEX™ or FORCE™ Biometric monitoring device 200 has a housing 202 that contains the electronics associated with the biometric monitoring device 200. A button 204 and a display 206 may be accessible/visible through the housing 202. A wristband 208 may be integrated with the housing 202.

Multimode Feature

When using a BMD to track physiological activities, the speed and accuracy of the measurement are affected by various factors, e.g., the device placement, the types of the activity the user engages in, and characteristics of the user's motion, etc. For instance, a user may be wearing a BMD on her wrist of her dominant hand for pedometry purposes. She may be running on a treadmill while holding a handle bar and flipping a magazine occasionally. This scenario presents challenges to conventional methods and devices that track steps and exploration. The fact that the user is holding the handle bar reduces the motion signal in her wrist that can be detected by the motion sensor of the BMD. Also, her occasional hand movements from flipping the magazine creates motion noise, which the BMD may mistakenly interpreted as steps.

In some embodiments, methods and devices are provided to overcome difficulties as in similar scenarios. In some embodiments, the BMD uses peak detection analysis for user activities that have high signal or signal-to-noise ratio (SNR), because peak detection analysis is often time and energy efficient, requiring less data and processing, as well as energy associated with the processing. Furthermore, the BMD uses periodicity analysis for activities that have lower signal or SNR, which is better at picking up relatively low signals and at filtering out motion noise that don't have regular temporal patterns. In some embodiments, the BMD has the function to automatically trigger various device modes to apply appropriate algorithms for analysis and processing. In some embodiments, signal periodicity is obtained by frequency domain analysis. In some embodiments, the signal periodicity may be obtained by time domain analysis. In some embodiments, frequency domain analysis and time domain analysis may be combined to obtain the periodicity.

Figure 3:
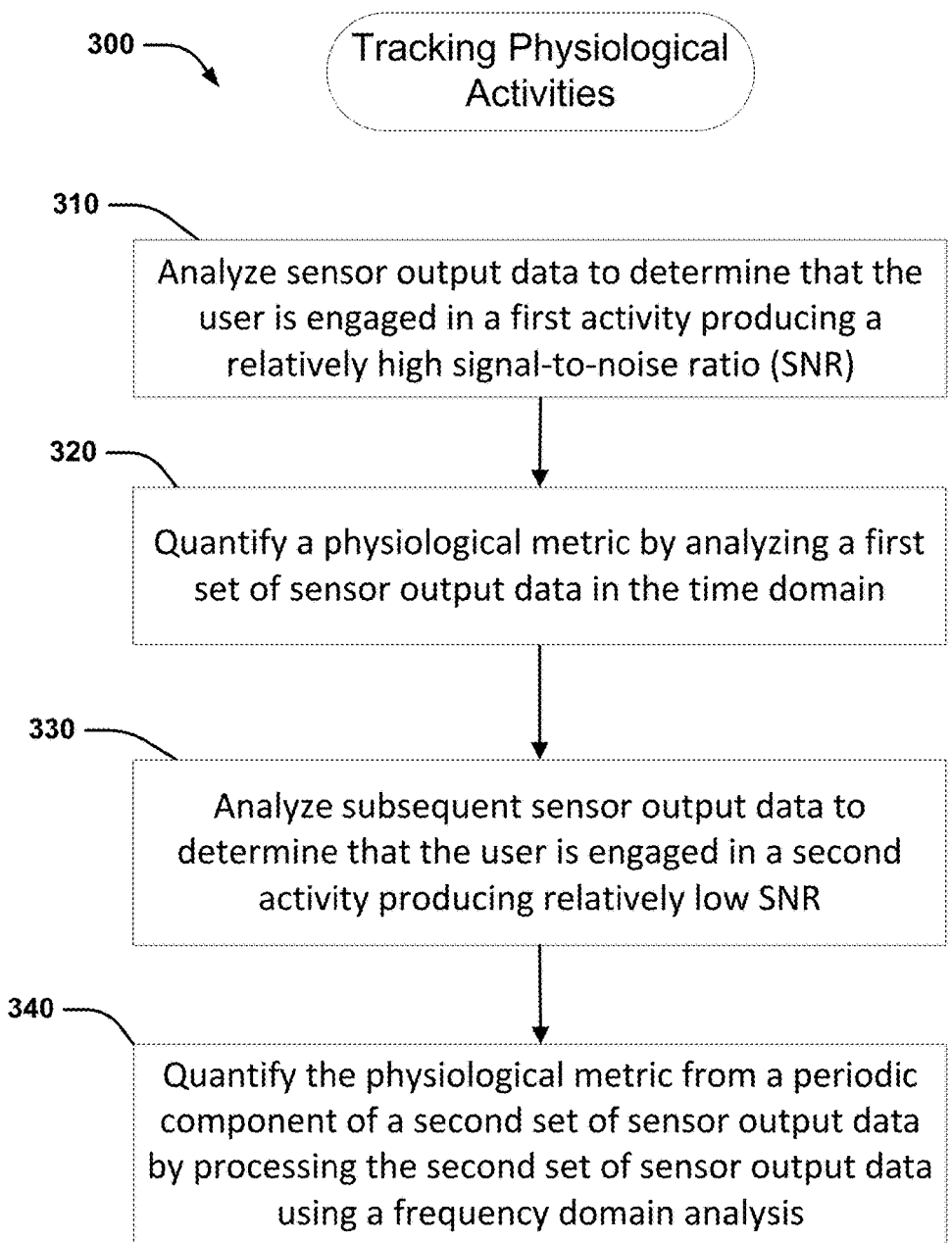
FIG. 3 shows a flow chart of a method for tracking a user's physiological activity according to some embodiments.

FIG. 3 shows a flow chart of method 300 for tracking a user's physiological activity according to some embodiments. The method uses a worn biometric monitoring device having one or more sensors to provide output data indicative of the user's physiological activity. Method 300 starts by analyzing sensor output data to determine that the user is engaged in a first activity that produces output data that has a relatively high SNR. See block 310. Method 300 proceeds to quantify a physiological metric, e.g., step count or heart rate, by analyzing a first set of sensor output data in the time domain. See block 320. In some embodiments, the BMD includes a motion sensor and the sensor output data includes amplitude of acceleration. In some of such embodiments, the time domain analysis may involve peak detection of acceleration. Method 300 also involves analyzing subsequent sensor output data to determine that the user is engaged in a second activity that produces a relatively low SNR in the subsequent sensor output data (in comparison to the prior sensor output data). See block 330. Furthermore, method 300 involves quantifying the physiological metric from a periodic component of a second set of sensor output data by processing the second set of sensor output data using a frequency domain analysis. See block 340. In some embodiments, the frequency analysis involves spectral analysis to detect spectral peaks and harmonics. In other embodiments, the frequency analysis applies a frequency band filter to the data, and then applies peak detection to the frequency filtered data to obtain periodic information in the second set of sensor output data. The peak detection algorithm may work on time domain data, albeit filtered in the frequency domain. In some implementations, SNR is not calculated, rather the sensor output data is characterized by a process that classifies in a manner indicative of SNR. For example, a classifier may be used to classify the data based on motion or signal strength by using input such as acceleration amplitude or power and other characteristics of accelerometer output.

Method 300 applies time domain analysis to data with relatively high signal (or SNR) and frequency analysis to data with relatively low signal. In certain embodiments, the method applies exclusively time domain analysis to the high SNR data and at least some frequency domain analysis to the low SNR data. In some embodiments, the BMD applies different motion intensity modes triggered by different motion intensity levels measured by a motion sensor, which reflects different user activity characteristics. The criterion that distinguishes the signal level for the two analyses should reflect different characteristics of the user's activity, e.g., running with hand moving freely vs. running with hand holding a bar. Different measures of motion may be used as the metric for determining motion intensity modes, such as SNR, signal norms, signal energy/power in certain frequency bands, wavelet scale parameters, and/or a number of samples exceeding one or more thresholds. Different values may be used set to as criteria for relatively low and relatively high signals. In some embodiments, a single value may be used to separates the first and second activity. In some embodiments, a third activity may be determined to have an activity level lower than the second activity (relatively low activity). The device may enter an inactive mode and not perform further analyses on the sensor output data.

In some embodiments, a sensor device can measure the user's activity intensity via pedometry. The sensor device can be implemented with single or multiple motion sensors that provide continuous or digitized time-series data to processing circuitry (e.g. ASIC, DSP, and/or microcontroller unit (MCU)). The processing circuitry runs algorithms to interpret the motion signals and derive activity data. In the case of a pedometer, the derived activity data comprises step counts. In some embodiments, the method analyzes motion data of multiple axis of a multi-axis motion sensor when the sensor output data signal is relatively low. In some embodiments, the method analyzes motion data of only a single axis of a multi-axis motion sensor when the sensor output data signal is relatively high, which improves time and energy efficiency in computing the physiological metric.

Categories of Modes

This subsection outlines the different types of modes. Sections hereinafter explain how various modes may be triggered, and how different modes apply different analyses and processes to derive biometric information. In some embodiments disclosed herein, BMDs have different kinds of modes that are triggered by different conditions and associated with different processing tailored for the conditions. In some embodiments, the device modes are provided in various categories: motion intensity modes, device placement modes, activity type modes, device state modes, etc. In some embodiments, some modes from the different categories may be combined for a particular condition. For instance, a semi-active motion intensity mode, a running activity type mode, and a dominant hand device placement mode may be combined for the scenario of running on treadmill when holding a handle bar described above.

Activity Type Modes

In some embodiments motion related activities are tracked by the BMD. In some embodiments, the BMD applies different processing algorithms the different activity types to provide speed and accuracy of biometric measurement and to provide activity specific metrics. For instance, BMD may provide elevation and route difficulty level in a rock climbing mode, but it may provide speed and cadence in a running mode.

In some embodiments, activity type modes may include, but are not limited to running, walking, elliptical and stair master, cardio exercise machines, weight training, driving, swimming, biking, stair climbing, and rock climbing.

Motion Intensity Modes

In some embodiments, there may be two or more different motion intensity modes. In some implementations, the BMD applies different processing algorithms to the different motion intensity modes to optimize speed and accuracy of biometric measurement and to provide activity specific metrics. In some embodiments, three motion intensity modes may be described in terms of three levels or ranges motion intensity measured by a motion sensor. These are sometimes loosely characterized herein as active mode, semi-active mode, and inactive mode. The algorithmic determinations of and the transitions between the modes, which enable step counting in a continuous manner and subsequent measurement of the user's biometric signals are further discussed herein. It should be noted that the three mode approach described herein is for illustration, and is not a limitation of the present inventions. There may be fewer modes (e.g., active and not active (e.g., car) in a two mode system) or greater than 3 modes. Indeed, the number of modes may vary depending on the user and the typical activities performed by the user. The number of modes may also change dynamically for each user depending on the likelihood of them to participating in certain activities. For example, a highly active mode may be disabled when a user is detected to be at work using a GPS. Description below provides further details about triggering events to enter different motion intensity modes. Often, the motion intensity modes are specific for a particular type of activity such as step counting.

Device Placement Modes

Sensor devices may infer users' activity levels algorithmically by processing the signal from sensors (e.g. motion, physiological, environmental, location, etc.). In the case of motion sensing, the signal can be affected by the placement of the sensor device. For example, motion signatures of the dominant hand and non-dominant hand are significantly different, leading to inaccurate estimation of activity levels from motion signals generated from the wrist, because users can choose to mount the sensor device on either hand and switch from one hand to another hand based on their needs. A set of modalities take different placements into account so that accurate and consistent biometric data measurement is enabled regardless of where users wear their sensor device.

Placement modes may include but are not limited to user's pocket, belt, belt loop, waistband, shirt sleeve, shirt collar, shoe, shoelaces, hat, bra, tie, sock, underwear, coin pocket, other articles of clothing, and accessories such as a helmet, gloves, purse, backpack, belt pack, fanny pack, goggles, swim cap, glasses, sunglasses, necklace, pendant, pin, hair accessory, bracelet, wristband, upper arm band and earring, and equipment such as skis, ski poles, snowboard, bicycle, skates, and skateboard. Additional modes may include those listed above with the additional specification of whether the location is on a dominant or non-dominant limb and/or left or right side of the user's body (e.g. wrist band on the dominant, right hand side of the user's body).

Monitor and Device State Mode

In some embodiments, the BMD has different monitor modes. A monitor is a tracking device mode that presents monitored information about a distinct physiological activity such as heartbeats or steps. A monitor as a device mode is different from an activity type mode as seen in a classic example of a heart rate monitor, which is not specific to an activity type. A heart rate monitor may measure and/or present the basic unit of cardiac activity (heartbeat) and/or increments of cardiac activity (heart rate). A tracking device may have multiple monitors, each with its own trigger and sensor data processing algorithm. Other device operations that may be specific to monitors include displayed content, display screen sequences, etc. A monitor may have sub-modes with their own triggers and data processing algorithms as discussed for activity type modes.

Device states are operational modes associated with various states of the hardware. Examples include a high/low battery mode, a syncing mode, timer mode, stopwatch mode, annotation mode, etc.

Triggers for Entering Activity Type Modes, Device Placement Modes, and Monitors

Manual Triggers

In some embodiments, users may manually trigger one or more modes of the BMD. In some embodiments, a user's direct interaction with the BMD (e.g., tap, push a button, perform a gesture, etc.) may trigger the device to enter particular activity type modes, device placement modes, and monitors. In some embodiments, a user may trigger the device to enter a mode by an interaction with a secondary device communicatively connected to the BMD as described herein after. For instance, a user may select an activity type mode from a list of options in a smart phone application or a web-browser.

The modes of the sensor devices can be selected manually by a user. Multiple methods can be considered in setting the most applicable mode in this case. In one embodiment, the mode selection may be wholly or partially determined from information gathered during sensor device pairing and from the user's online account. Each sensor device may be paired with an online account or secondary computing device such as a smartphone, laptop computer, desktop computer, and/or tablet which enables entry of and stores user-specific information including but not limited to the user's placement preference. This user-specific information may be communicated to the user's activity monitoring device, via a wireless or wired communication protocol. For example, in embodiments where the sensor device may be worn on either wrist, the user may select a dominant or non-dominant hand setting to tune the biometric algorithms for the wearing location.

In some embodiments, the placement or activity type mode can be set through a user interface on the device. The user can set the mode through an interface that includes the display, button(s), and/or touch screen. The mode selection may be stored in local storage of the device or in a secondary electronic device in communication with the sensor device including but not limited to a server.

Hand gestures observed via motion sensors can be used to set such modes as well. There can exist one-to-one correspondence to a mode with a hand gesture so that a particular hand gesture (e.g., waving the device) triggers a mode. In addition, a sequence of hand gestures can be used to enter a mode, e.g., hand-waving motion followed by a figure eight motion. In these cases, the user may receive a confirmation of the mode through a secondary sensual stimulation such as a play pattern of a vibration motor, or LED's.

Automatic Triggers

In addition to manual mode set-up, automated algorithms (e.g. machine learning) can be applied to detect the placement and/or activity type. In some embodiments, tracking device sensor output contains a detectable activity type signature. The BMD may automatically detect the activity type signature and trigger the BMD to enter an activity type mode corresponding to the activity type signature. In some embodiments, a BMD interacts with an external signal that triggers the BMD to enter an activity type mode or a monitor. The external signal may be provided by, e.g., RFID tag or other short range communication probe/signal affixed to activity type related objects such as a bicycle handle or a climbing hold. In some embodiments, the external signal may be provided by the environment such as ambient light intensity.

In some embodiment, an automatic trigger is implemented using motion sensors only. Signatures of motion signals are significantly different depending on the placement of the sensor device. Even at the same placement location, each user's activities will be registered in motion signals that have different characteristics in time domain as well as a transformed domain (including but not limited to the spectral domain). Therefore, a machine learning classification technique (e.g. decision tree learning, Hidden Markov Model (HMM) and Linear Discriminant Analysisis) may be considered for this supervised learning. For off-line training, the data are collected and annotated according to the placement of the sensor device and activity type of users. Features are then extracted from the data in the time-domain as well as its transformed representations including but not limited to Fourier transform and wavelet transform. The features are then used to train coefficients that determine the decision rules. This set of coefficients may be trained offline (e.g. on a cloud in post processing). The set of coefficients are then incorporated into the embedded system of the sensor device so as to determine user's device placement location and activity type.

In some embodiments, additional sensors can be used in addition to motion sensors to detect activities. Additional sensors may include, but are not limited to those further described hereinafter. The activity types can be statistically inferred from signals from the additional sensors with or without motions signals. For example, an HMM can be utilized where the hidden states are defined to be the physical activities, and the observed states are subset or all of the sensor signals. An example of using an additional sensor for automatic trigger of an activity type mode is automated swimming detection via pressure sensor by detecting a steep pressure increase or high pressure. GPS data or GPS signal in combination with some signatures in motion signals can be statistically modeled to detect user activities whose speed is a desirable metric of the activity (e.g. driving and biking).

In some embodiments modes may be automatically or semi-automatically (e.g. one or more, but not all steps of selecting a mode are automatically performed) selected with the use of a short range wireless communication as described in U.S. patent application Ser. No. 13/785,904, titled "Near Field Communication System, and Method of Operating Same" filed Mar. 5, 2013 which is entirely incorporated herein by reference. In some embodiments, a radio device can be placed at a specific location associated with the activity to be detected. For instance, an NFC chip can be attached to gym equipment. A gym user can tag the gym equipment with her NFC enabled sensor device before and after the specific exercise. In one embodiment the NFC chip mounted on the gym equipment may also transmit exercise data gathered from the gym equipment that can be used to correct and/or improve activity data measured by the sensor device.

Even during an activity, the radio devices can be used to track intensity and efficiency of the activity. One implementation of this idea relates to NFC equipped holds for indoor climbing (e.g. rock climbing). A climber must contact their hands and feet to the holds to climb up, as well as the initial holds and final hold that define a route (a route is a predefined area, path, and/or set of holds which can be used in a climb and is typically given a rating corresponding to its difficulty). The sensor device or devices mounted on the users' hands, feet, and or other body parts communicate with NFC chips placed in or near the holds. The information collected via the sensor devices are processed in the sensor device(s) and/or a cloud computing system to provide a better understanding of the activity to the users. See Section 4.a for detailed implementations and embodiments.

Pre-existing radio equipment can be utilized to detect a user activity. Modern cars are often equipped with Bluetooth (BT) technology. The sensor device enabled with BT can pair with the car through BT communication protocol. Once the monitoring device and car are paired to each other, a walk-in to the car will prompt syncing between the two, and the car will be able to transmit status and information on the user's activity (e.g. driving for n hours at x mph).

Triggers for Entering Motion Intensity Modes

Manual Triggers

Similar to activity type modes and device placement modes, motion intensity modes may also be triggered by user interaction with the tracking device (e.g., tap, push a button, execute a gesture, etc.) or with a secondary device (e.g., select in a smart phone application).

Automatic Triggers

In some embodiments, a tracking device or BMD's sensor output contains a detectable motion intensity signature. This motion intensity signature may be detected by the BMD and triggers the device to enter various motion intensity modes. Combinations of sensor outputs may be used. The input to the trigger algorithm may come directly or indirectly from the sensor output. For example, the input may be direct output from an accelerometer or it may be processed accelerometer output such as a "sleep state" described below.

Figure 4A:
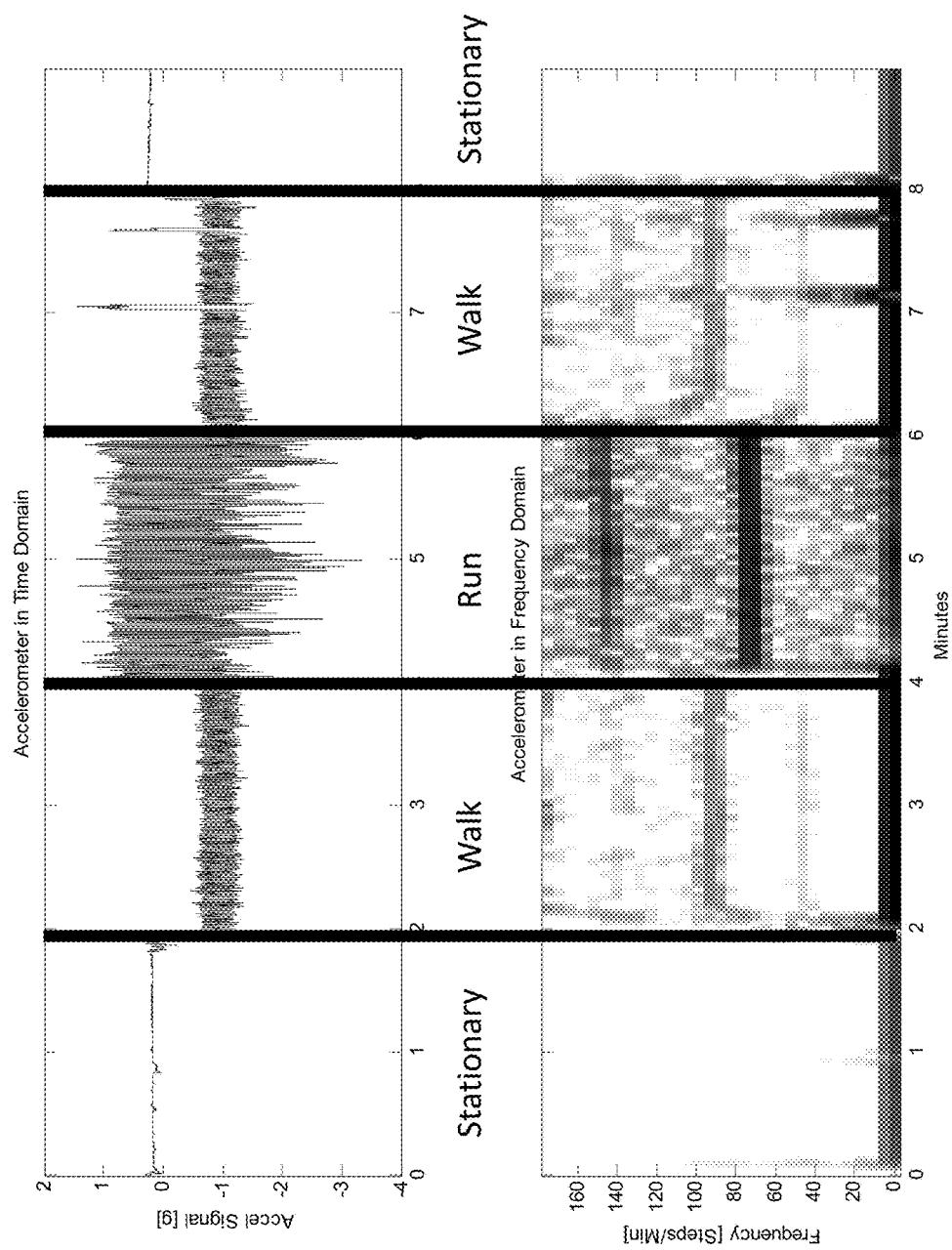
FIG. 4A shows acceleration data in time domain (top panel) and frequency domain (bottom panel) for stationary, walking, and running activity for a user.
Figure 4B:
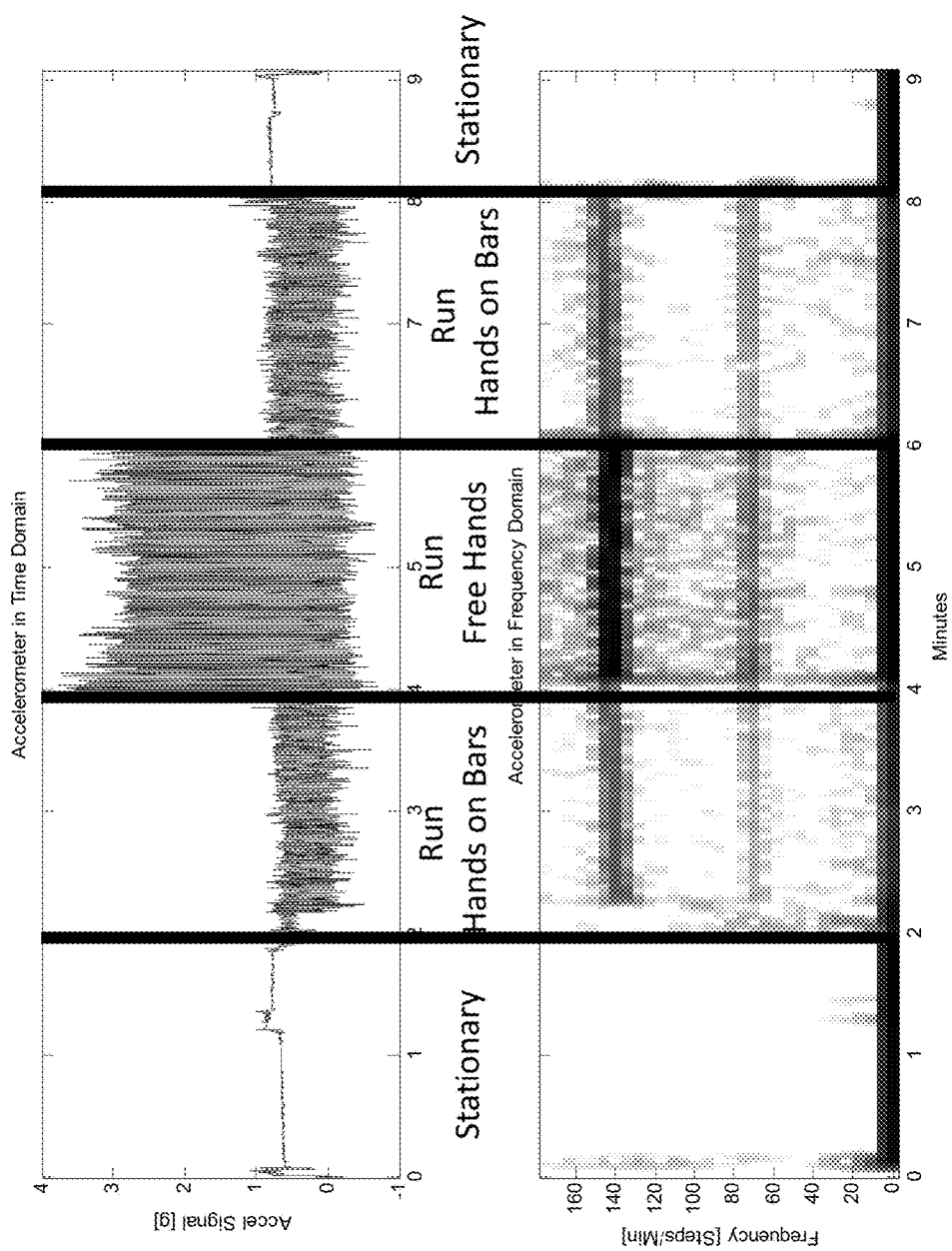
FIG. 4B shows similar data for stationary, running with hands on bars, and running with free hands.

As explained above, certain activity characteristics are associated with different levels of motion intensity detected by a motion sensor of a BMD worn by a user. In some conditions, a user is engaged in a moving activity, but the user's limb wearing the BMD has reduced motion or limited acceleration as compared to a regular moving activity with freely moving limbs. For instance, the user may be running on a treadmill while holding a bar, walking while pushing a shopping cart, or walking when carrying a heavy object. In such conditions, the motion intensity detected by the motion sensor may be greatly reduced. This is illustrated with data shown in FIGS. 4A-B. FIG. 4A shows acceleration data in time domain (top panel) and frequency domain (bottom panel) for stationary, walking, and running activity for a user. FIG. 4B shows similar data for stationary, running with hands on bars, and running with free hands. The top panel of FIG. 4A shows that running produces higher acceleration signal than walking, which is in turn higher than stationary. The top panel of FIG. 4B shows that running with free hands produces the highest level of signal intensity, which is higher than running with hands on bars, which is higher than stationary. Notably, running with hands on bars causes the acceleration signal to become more irregular and noisier as compared to walking. With this lower signal level and/or higher noise when running with hands on bars, it becomes difficult to use peak detection analysis of time domain data to obtain step counts. In some conditions, the BMD automatically analyses motion signal provided by a motion sensor, and automatically switches motion intensity modes, which deploy different data processing algorithms to process motion data.

In one embodiment, the device can determine a mode of the device using the motion sensor signal strength. The motion sensor signal strength can, for instance, be determined by signal-to-noise ratio, signal norms (e.g. L1, L2, etc.), signal energy/power in certain frequency bands, wavelet scale parameters, and/or a number of samples exceeding one or more thresholds. In some embodiments, accelerometer output power is used to determine different motion intensity modes, where the power is calculated as a sum of accelerometer amplitude values (or amplitude squared values). In some embodiments, data from one axis, or two axes, or three axes of one or more motion sensor may be used to determine the motion intensity. In some embodiments, data from one axis are used for further analyses when the signal is relatively high, while data from two or more axis are used for further analyses when the signal is relatively low.

A motion intensity mode may be activated when the motion level is within a certain range. In the case of a pedometer sensor device, there may be three different motion level ranges corresponding to three modes; active mode, semi-active mode, and inactive mode. The algorithmic determinations of and the transitions between the modes, which enable step counting in a continuous manner and subsequent measurement of the user's biometric signals are further discussed below. It should be noted that the three mode approach described herein is for illustration, and is not a limitation of the present inventions. There may be fewer modes (e.g., active and not active (e.g., car) in a two mode system) or greater than 3 modes. Indeed, the number of modes may vary depending on the user and the typical activities performed by the user. The number of modes may also change dynamically for each user depending on the likelihood of them to participating in certain activities. For example, a highly active mode may be disabled when a user is detected to be at work using a GPS.

In some embodiments, in addition to or instead of real time or near real time motion sensor data, previously processed and/or stored sensor information may be used to determine a motion intensity mode. In some embodiments, such previous information may include a record of motion information for a previous period (e.g., 7 days) at a fixed time interval (e.g., once per minute). In some embodiments, the previous information includes one or more of the following: a sleep score (awake, sleeping, restless, etc.), calories burned, stairs climbed, steps taken, etc. Machine learning may be used to detect behavior signatures from the prior information, which may then be used to predict the likelihood of a subject has certain activity levels at the present time. Some embodiments use one or more classifiers or other algorithm to combine inputs from multiple sources (e.g., accelerometer power and minutely recorded data) and to determine the probability that the user is engaged in an activity with certain characteristics. For instance, if a user tends to be working at a desk at 3 PM but doing shopping at 6 PM, the prior motion related data will show data pattern reflecting the user's tendency, which tendency can be used by the BMD in a classifier to determine that the user is likely walking while pushing a shopping cart at the present time at 6:15 PM today.

In some embodiments, a clustering algorithm (e.g. k-means clustering, nearest neighborhood clustering, and expectation maximization) may be applied to classified modes based on a-priori knowledge that users are probably doing each activity (e.g., driving) for continuous periods of time.

In some embodiments motion intensity modes may be automatically or semi-automatically selected with the use of a short range wireless communication as described above for automatic selection of activity type modes and device placement modes.

Sensor Data Processing Distinctions-Activity Type Modes, Device Placement Modes, and Monitors Users perform many types of activities over the course of the day. However, the sensor device is not necessarily optimized for all the activities. Knowing the activity of a user for a given time enables a sensor device to run one or more algorithms that are optimized for each specific activity. These activity specific algorithms yield more accurate data. According to some embodiments, in each activity type mode, different data processing algorithm may be applied to improve activity metric accuracy and provide activity-specific biometrics.

A user may wear the BMD at different positions. Device placement modes may be set manually or automatically as described above. In each device placement mode, placement-specific algorithms are run in order to estimate biometrics of interest more accurately. A variant of the placement-specific algorithms may be an adaptive motion signal strength threshold that changes its value according to expected movements of the body part. Adaptive filtering techniques may be used to cancel out excessive movements of the body part using the placement mode as a priori. Pattern recognition techniques such as support vector machine or Fisher's discriminant analysis can also be used to obtain placement-specific classifiers, which will discern whether or not a signal or signatures of the signal are representative of the biometrics of interest.

Sensor Data Processing Distinctions-Motion Intensity Mode

Time Domain Analysis

In some embodiments, the BMD applies algorithms that process data in the time domain. This is especially useful when for data with easy to identify basic units of physiological activity in the time domain. This is typically used for data with high signal or SNR. In some embodiments, the time domain analysis includes peak detection of motion amplitude data (e.g., acceleration). Returning to the example data discussed above and shown in the top panels of FIGS. 4A-B, one can see the conditions when motion signal or SNR is large in conditions when the user is talking or running with free hands. In conditions like these, a BMD employs time domain analyses according to some embodiments.

In many embodiments, the time domain analysis is more time and energy efficient as compared to frequency domain analysis further described below, which is suitable for data with insufficient signal or SNR. Peak detection of motion data usually requires less amount of data to be analyzed as compared to frequency analysis, therefore it has a lower demand for data amount and analyses. In various embodiments, the peak detection operation may be performed using data collected from a duration in the order of magnitudes in seconds. In some embodiments, the range of data duration is about 0.5-120 seconds, or 1-60 seconds, 2-30 seconds, or 2-10 seconds. In comparison, in some embodiments, a frequency analysis may use data of a longer duration than data used in peak detection.

In one embodiment, a time-domain analysis can be applied to data of relatively low signal or SNR to find features associated with periodicity and/or the period of the buffered motion sensor signal. These analyses may include, but are not limited to auto regression analysis, linear prediction analysis, auto regression moving average analysis, and auto/partial correlation analysis. One or more threshold rules and conditional decision rules are then applied on the features and/or the coefficients of the analysis to detect periodicity and estimate the period, and subsequently biometrics of the user.

Frequency Domain Analyses

In some embodiments, algorithms operating in the frequency domain are used when time domain sensor data does not contain easy to identify basic units of physiological activity. The problem often occurs because the periodic signals have relatively low amplitude and a peak detection algorithm may be insufficiently reliable. One example is step counting with the tracking device on a user's wrist while the user is pushing a stroller or shopping cart. Another example is step counting while the user is on a treadmill or bicycling. Another example is step counting while a user is in a car. In this case, the frequency domain analysis helps us avoid counting steps when the user moves due to vibration of the ride such as when the car runs over a bump. A third example is when the user is walking while carrying a heavy object with the limb wearing the BMD.

Referring to the example data discussed above and shown in the top panels of FIG. 4B, acceleration signal or SNR is small when the user is running with hands on bars. It is difficult to use peak detection with the data in shown in the top panel because the data is noisy and the peaks are not reliable. However, the frequency components show spectral peaks at about 65 Hz and 130 Hz in the bottom panel of FIG. 4B in the two subpanels for running with hands on bars. In conditions like these, a BMD employs frequency domain analyses according to some embodiments.

As mentioned above, a frequency analyses may use data buffered for a longer duration than data used in peak detection. In some embodiments, the range of data duration for frequency analysis is in the order of magnitudes in seconds to minutes. In some embodiments, the range is about 1 second to 60 minutes, 2 seconds to 30 minutes, 4 seconds to 10 minutes, 10 seconds to 5 minutes, 20 seconds to 2 minutes, or 30 seconds to 1 minute.

In some embodiments, the length of buffered motion signal may be set depending on the desired resolution of the classification. Each application of selection algorithms using motion intensity modes to this buffered motion signal returns a classified mode (e.g. semi-active and driving mode) and step (cadence) counts for the segment of the motion signal. Post processing may then be applied onto these resultant values in the processing circuitry of the sensor device and/or remote processing circuitry (e.g. cloud server). In one embodiment, a simple filter can be applied to the estimated steps (cadences) so as to remove a sudden change in step (cadence) counts. In another instance, a clustering algorithm (e.g. k-means clustering, nearest neighborhood clustering, and expectation maximization) may be applied to the classified modes based on a-priori knowledge that users are probably doing each activity (e.g., driving) for continuous periods of time. These updated modes from clustering are then used to update steps (cadences) for the given buffered motion signal.

In some embodiments, the BMD may have an active mode, a semi-active mode, and an inactive mode for motion intensity modes. In the active mode, the motion sensors of the sensor device detect acceleration, displacement, altitude change (e.g. using a pressure sensor), and/or rotations which can be converted into step counts using a peak detection algorithm. In inactive mode, the user is sedentary (e.g., sitting still) and the pedometer (via the motion sensors) does not measure any signals which have the signature of steps. In this case, no further computations are performed to detect steps. In semi-active mode, the motion sensors observe some of the user's movements, but the motion signals do not possess enough strong signatures of steps (e.g. a sequence of high amplitude peaks in a motion sensor signal that are generated by steps) to be able to accurately detect steps using the peak detection algorithm.

In semi-active mode, time- and/or frequency-domain analysis may be performed on the buffered motion signal of a certain length to find features associated with periodic movements such as steps. If any periodicity or features representing periodicity of the buffered motion signal are found, the period is estimated and then interpreted as biometrics of the user such as the average step rate of the buffered motion signal.

Frequency domain analysis could include techniques other than just using FFT or spectrograms as illustrated in FIGS. 4A and 4B. For example, a method may involve first band passing the time domain signal, and then running a peak counter in the time domain. Other methods may be used to process data with frequency analyses, and the processed data may then be further process to obtain periodicity or peak of signal.

In some embodiments, frequency-domain transformation/analysis may be performed on the buffered motion signal using techniques including but not limited to Fourier transform, e.g., fast Fourier transform (FFT), cepstral transform, wavelet transform, filterbank analysis, power spectral density analysis and/or periodogram analysis. In one embodiment, a peak detection algorithm in the frequency domain may be performed to find spectral peaks that are a function of the average step rate of the buffered motion signal. If no spectral peaks are found, the algorithm will conclude that the user's movements are not associated with ambulatory motion. If a peak or a set of peaks are found, the period of the buffered motion signal is estimated, enabling the inference of biometrics. In another embodiment, a statistical hypothetical test, such as Fisher's periodicity test is applied to determine if the buffered motion signal possess any periodicity and subsequently, if it possess biometric information associated with the user's activity. In yet another embodiment, the harmonic structure is exploited to test periodicity and/or estimate the period. For example, a generalized likelihood ratio test whose parametric models incorporate harmonicity of the buffered motion signal may be performed.

In another embodiment, a set of machine-learned coefficients can be applied onto a subset of frequency- and/or time-domain features that are obtained from frequency- and/or time-domain analysis described above. A linear/non-linear mapping of an inner product of the coefficients and the subset of spectral features then determines if the given buffered motion signal is generated from a user motion that involves some periodic movements. The machine learning algorithm classifies motion signals into two categories: signals generated from steps and signals generated from activities irrelevant to steps.

With this semi-active mode algorithm, for example, steps can be detected even when the user is wearing the sensor device on his/her wrist and holding the handle bars of a treadmill while he/she is walking on the treadmill. In the case that the buffered motion signal does not have the signature of ambulatory motion, the buffered motion signal may be disregarded without counting any steps to eliminate the chance of incorrectly counting steps. For example, the motion signal of a user driving over a bumpy road in the time domain will show a series of peaks of high amplitude which have a signature similar to that of steps. A peak detection pedometer algorithm run on the time domain motion signal of driving on a bumpy road would cause the pedometer to count steps when it should not. However, in the frequency-domain and/or in signals to which an appropriate time-domain analysis is applied, the same motion signal of driving on a bumpy road is unlikely to have signatures associated with ambulatory motion (e.g. signatures of periodicity). When signals represented in frequency domain and/or signals to which a time-domain analysis is applied do not have a signature of ambulatory motion, steps are not counted as it can be assumed that the user is not actually walking or running.

Example-Motion Intensity Modes for the Walking/Running Activity Type

Figure 5A:
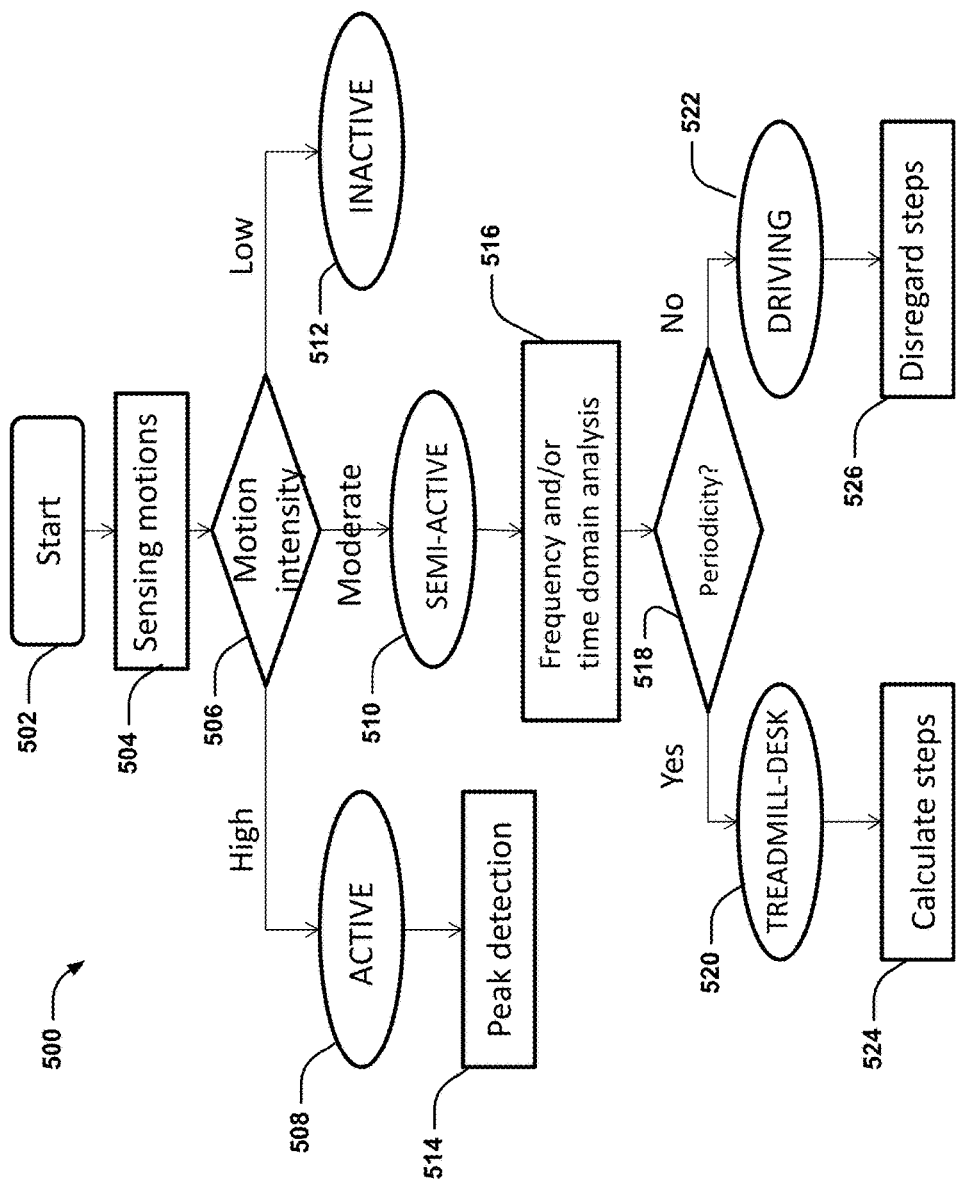
FIG. 5A is a flowchart showing a process for tracking step count using a BMD according to some embodiments.

FIG. 5A is a flowchart showing process 500 for tracking step count using a BMD according to some embodiments. The process automatically selects motion intensity modes, and applies different data processing algorithms for different motion intensity modes. The BMD has one or more sensors providing data indicative of the user's physiological activities, including motion data indicative of steps. The BMD senses motion of the user using one or more motion sensors, which sensors are described further below. See block 504. The BMD analyzes motion data provided by the motion sensor to determine the motion intensity that is caused by the user's activity. See block 506. In some embodiments as illustrated here in FIG. 5B, the BMD determines three ranges of motion intensity: high, moderate, and low, respectively associated with an active mode, a semi-active mode and an inactive mode. In some implementations, the active mode corresponds to a user running or walking with freely moving hands; the semi-active mode corresponds to the user running or walking on a treadmill while holding fixed handlebars, typing at a desk, or driving on a bumpy road; and the inactive mode corresponds to the user being stationary.

As stated above, some embodiments may employ more or fewer than three motion ranges corresponding to more or fewer than three modes. The specific ranges of the different modes may defer for different applications or different users. The specific ranges may be supplied by off-line prior knowledge in some embodiments. In some embodiments, the specific ranges may be influenced by machine learning process that selects the ranges having the best speed and accuracy for step count calculation.

In process 500, if the BMD determines that the user is engaged in an activity that allows the motion sensor to measure high motion intensity, the BMD may enter an active motion intensity mode. See block 508. In some embodiments, in addition to current motion data, the BMD can also use other forms of motion related data in its analysis to determine the motion intensity modes. For instance, in some embodiments, the BMD can receive prior data previously processed and/or store. Such data may include sleep quality, step counts, calories burned, stairs climbed, elevation or distance traveled, etc. as described above. In some embodiments, the prior data were recorded at fixed intervals, such as every minute, every 10 minutes, every hour, etc. The BMD may use one or more classifiers to combine the current motion intensity signal and the prior motion related data to determine that the user is likely to be engaged in an activity producing high motion intensity signal, which determination triggers the BMD to enter an active mode as a motion intensity mode. The BMD then applies a peak detection algorithm to analyze the motion data. See block 514. The detected peaks and associated temporal information provide data to calculate step count.

In some embodiments, the BMD may determine that the motion intensity from the motion sensor data is moderate as described above, then triggers the BMD to enter the semi-active mode. See block 510. The motion intensity range used to define the semi-active mode may be lower than the active mode and higher than the inactive mode. In some embodiments, the BMD applies frequency domain analysis and/or time domain analysis to detect periodicity in the motion data. See block 516. In some embodiments, the BMD applies FFP to obtain frequency information of the motion signal. Other frequency domain analysis and time domain analysis described above are also applicable here. Using information derived from the frequency domain or time domain analysis, the BMD decides whether the data contains periodic information. See block 518. If yes, the BMD infers that the motion data is produced by the user engaging in walking or running on the treadmill, or some other activities with periodic movements of the limb wearing the BMD, such as typing at a desk. See block 520. In some embodiments, the BMD may further apply one or more filters or classifiers to determine whether the periodic information is related to stepping action as further described below. If so, the BMD calculates a step count using the periodic information, e.g., a 1 Hz periodic motion lasting for 10 seconds corresponds to a cadence of 60 steps per minute and 6 steps. See block 524. If the DND determines that there is no periodic information in the motion data, infers that the user is engaged in activities with the regular motion, such as driving on a bumpy road. See block 522. In some embodiments, the BMD may disregard any step counts that may have otherwise accumulated during the corresponding period (e.g. steps from time domain analysis).

The BMD may enter into an inactive mode when motion intensity level is low. See block 512. The inactive mode may correspond to the user being stationary. In some embodiments, the BMD does not further process the motion data when it is in an inactive mode.

Figure 5B:
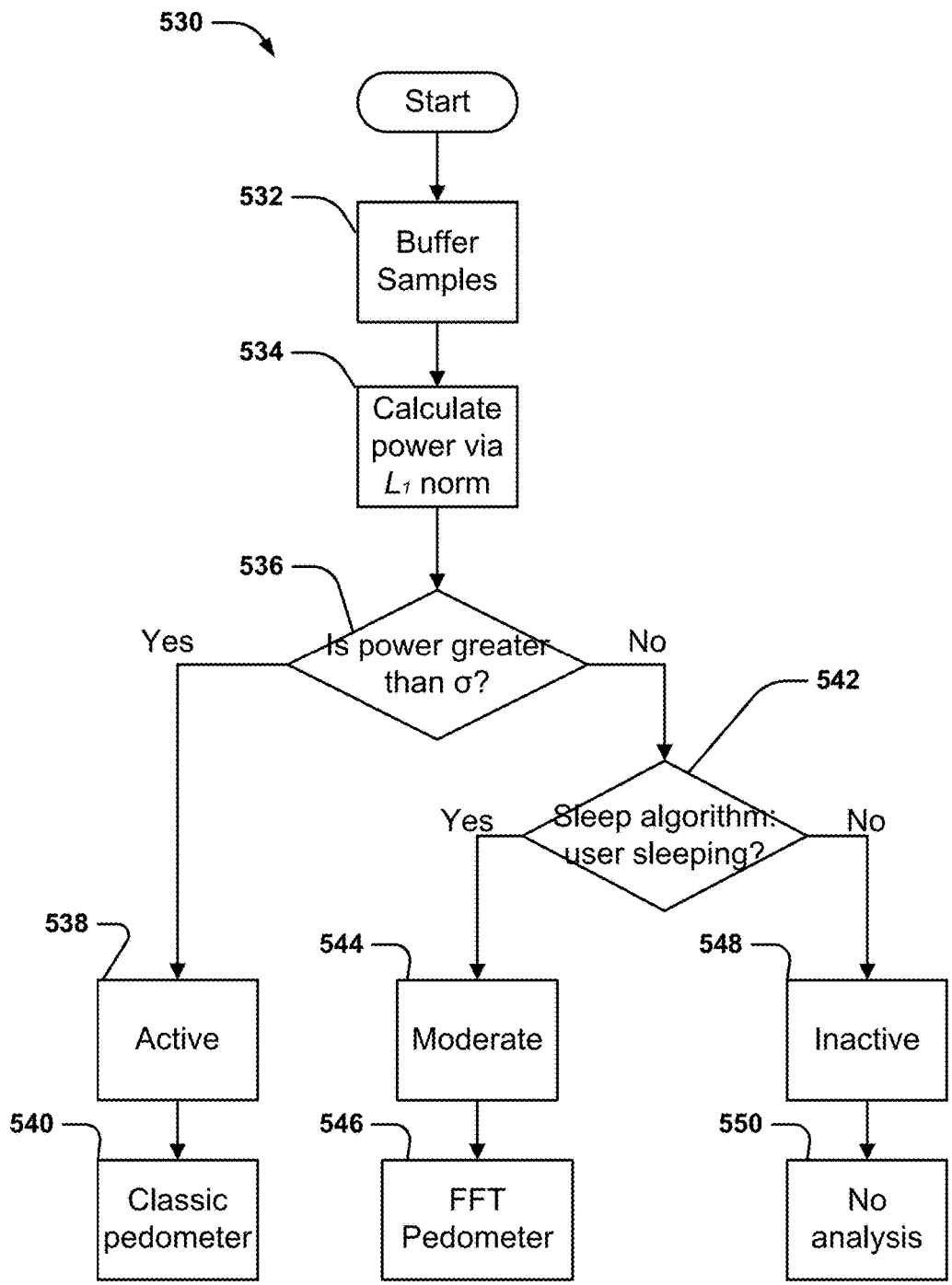
FIG. 5B shows a process for determining three ranges of motion intensity modes according to some embodiments.

FIG. 5B is a flowchart showing process 530 for a BMD to automatically select modes for different user activity conditions according to some embodiments. The different modes then apply different analysis to obtain step counts. Process 530 may be implemented as a sub-process of process 500. Process 530 for switching modes uses motion intensity detected by motion sensor and previously analyzed and/or recorded motion related information. In the embodiment shown here, the previous information is processed by a sleep algorithm. Process 530 starts with buffering samples of motion data. The amount of data buffered may depend on different applications and conditions. In the process shown here, current motion data is buffered to determine whether the device should enter one of the motion intensity modes. This data for triggering different motion intensity modes may be the same or different from the data that is used to analyze steps in the different modes. The duration of these two kinds of data may also be the same or different. In some embodiments, the BMD continuously buffers data samples in order to determine whether to select, maintain, and/or change motion intensity modes. The process proceeds to calculate the power of signal from the buffered sample. In some embodiments the calculation is based on $I_1$ norm, i.e. sum of the absolute values of the signal. See block 534.

Process 530 continues by determining whether the power of the signal is greater than an empirically determining threshold σ as shown in block 536. The threshold may be trained by machine learning algorithms in some embodiments to improve the algorithm for selecting the different modes, the machine learning training allows the BMD to obtain accurate step counts with high efficiency. In some embodiments, the empirically determined threshold may be adjusted by the user or by knowledge based on other users. If the process determines that the power of the signal is greater than the empirical threshold σ, the BMD is triggered to enter into an active mode. See block 538. Then the BMD performs step counting analysis in a manner similar to a classic pedometer as described above using peak detection method. See block 540. If the process determines that the signal power is not greater than the empirical threshold σ, then in some embodiments, it uses a sleep algorithm to further analyze if it should enter into a moderate or inactive mode. In some embodiments, the sleep algorithm analyzes prior motion related information to determine whether the user is likely to be asleep, awake, or moving when awake. In some embodiments, the prior motion related information may be information derived from motion, such as step counts, stairs climbed, etc., as further described herein. In some embodiments, if sleep algorithm determines that the user is likely sleeping, then it enters into an inactive mode. See block 548. In some embodiments, the BMD in the inactive mode performs no further analysis of the sensor signal, which may help preserve battery of the BMD. See block 550. However if the sleep algorithm determines that the user is not sleeping, then the BMD enters into a moderate motion intensity mode. See block 544. The BMD performs an FFT analysis of motion data in the frequency domain to determine steps. Examples of some applicable frequency analyses are further described hereinafter.

Figure 6A:
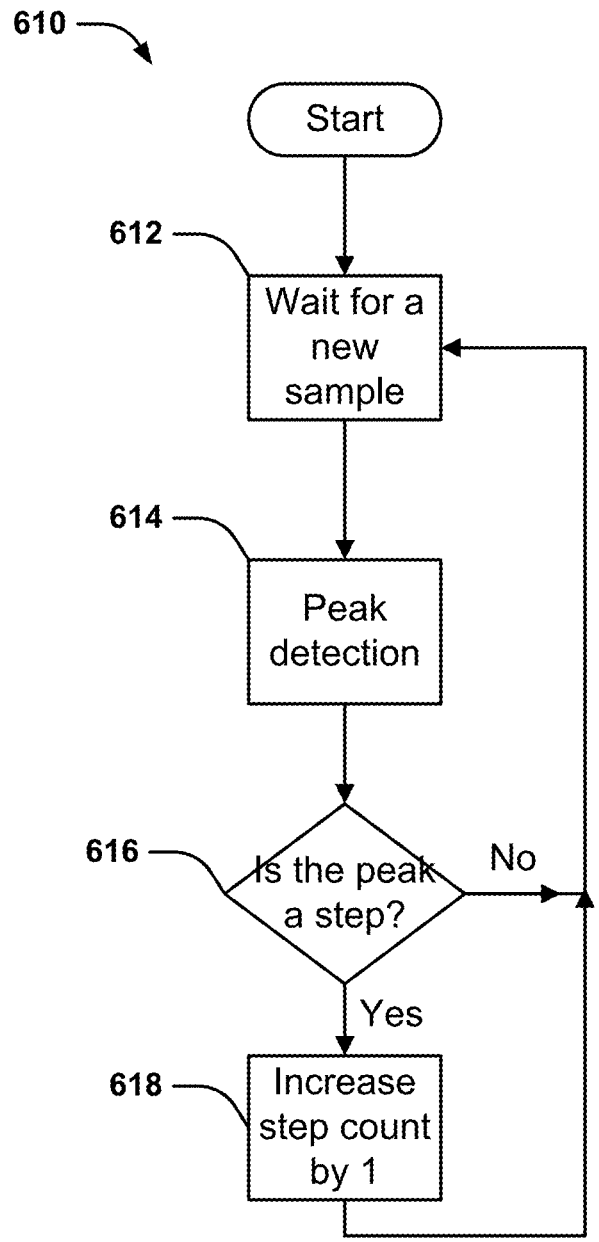
FIG. 6A is a flowchart showing a process to implement peak detection to calculate step count under an active mode according to some embodiments.

In some embodiments, the BMD may implement the peak detection operation of 514 under active mode using process 610 shown in FIG. 6A. The process to implement peak detection to calculate step count in process 610 starts with obtaining a new sample of motion data such as acceleration data. In some embodiments, a sample is a digitized value recorded by a sensor that is approximately linear to an analog signal to be measured. In some embodiments, the analog signal is acceleration (e.g., m/s$^2$). The duration of the sample may be chosen based on different considerations as described above. In some embodiments, the new sample includes acceleration data for a duration of about 0.5-120 seconds, or 1-60 seconds, 2-30 seconds, or 2-10 seconds.

Figure 6B:
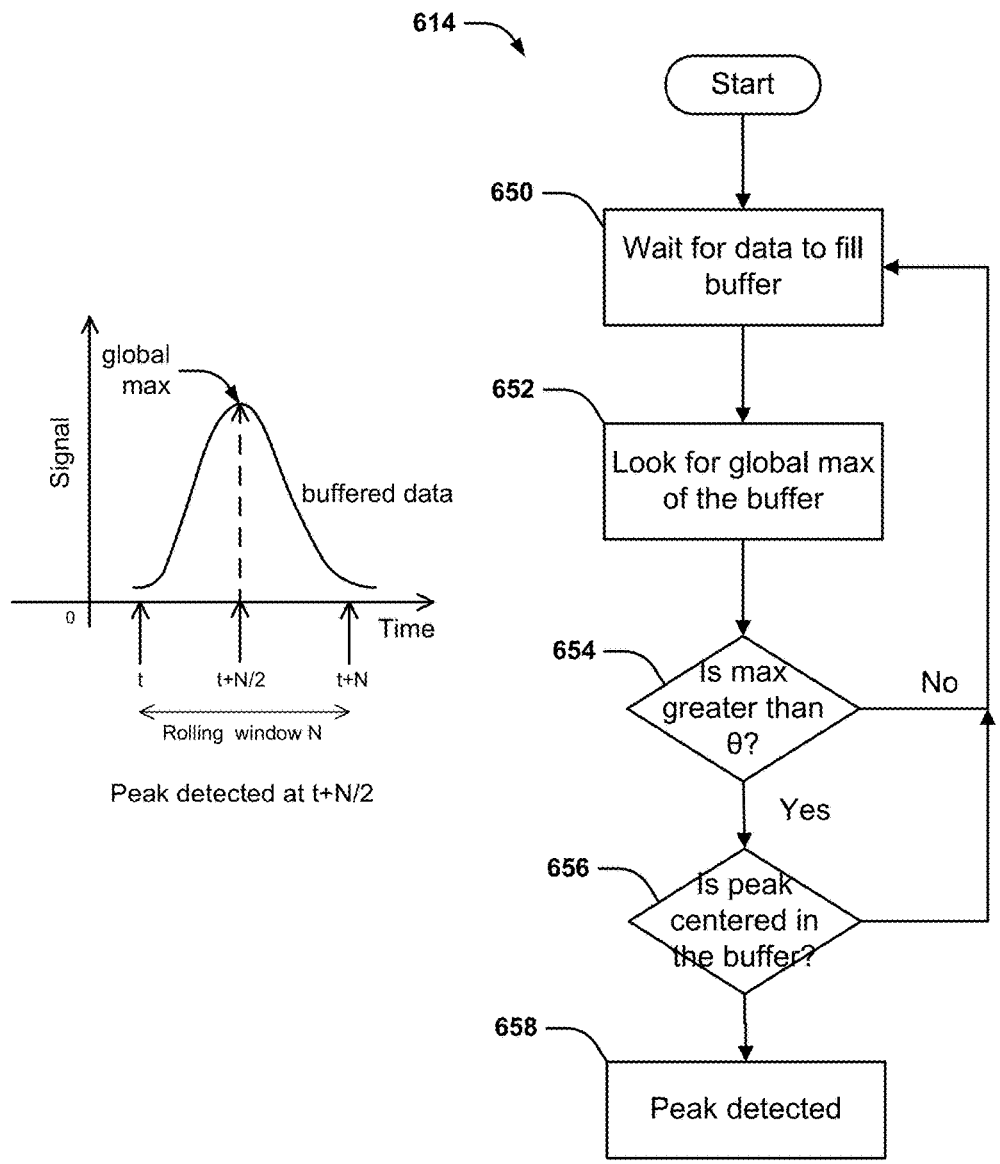
FIG. 6B is a flowchart showing a process that may be used to implement peak detection according to some embodiments.

The process then performs a peak detection analysis. See block 614. FIG. 6B shows a process that may be used to implement peak detection performed in block 614 according to some embodiments. The process starts by waiting for data to fill a data buffer described above. See block 650. Then the process involves looking for a global maximum of the buffered data. See block 652. As shown in the diagram to the left of block 652, some embodiments may apply a rolling time window of duration N, which duration may be chosen as described above. The roller time window's starting and ending time may be designated as t and t+N as shown in the figure. The process searches for the global maximum of the data in the rolling window. After the global max is computed, the process determines whether the global max is greater than an empirically determined threshold θ. See block 654. If the global maximum is not greater than the empirical threshold, then the process reverts to waiting for new data to fill the buffer as shown in operation 650. If the global maximum is greater than the threshold, the process further determines whether the global maximum occurs at or near the center of the rolling time window. It the maximum is not at or near the center of the time window, the process determines that the peak is likely not a step, therefore the process reverts to waiting for new data to feel the buffer is in operation 650. If the peak is centered on the buffered time window, the process determines that a peak is detected at or near t+N/2.

An alternative process may be applied for peak detection analysis, which involves calculating the first derivative and finding any first derivative with a downward-going zero-crossing as a peak maximum. Additional filters may be applied to remove noise from detected peaks. For instance, the presence of random noise in real experimental signal will cause many false zero-crossing simply due to the noise. To avoid this problem, one embodiments may first smooth the first derivative of the signal, before looking for downward-going zero-crossings, and then takes only those zero crossings whose slope exceeds a certain predetermined minimum (i.e., "slope threshold") at a point where the original signal exceeds a certain minimum (i.e., "amplitude threshold"). Adjustment of the smooth width, slope threshold, and amplitude threshold can significantly improve peak detection result. In some embodiments, alternative methods may be used to detect peaks. Process 610 then proceeds to analyze whether the peak is associated with a step. See block 160. This analysis may be performed by applying one or more classifiers or models. If the analysis determines that the peak is not associated with a step, the process returns to obtaining a new sample as shown in block 612. If the analysis determines that the peak is associated with a step, then the process increases the step count by 1. See block 618. Then the step counting process returns to obtaining a new sample shown in block 612. The step counting process continues on in the same manner.

Figure 6C:
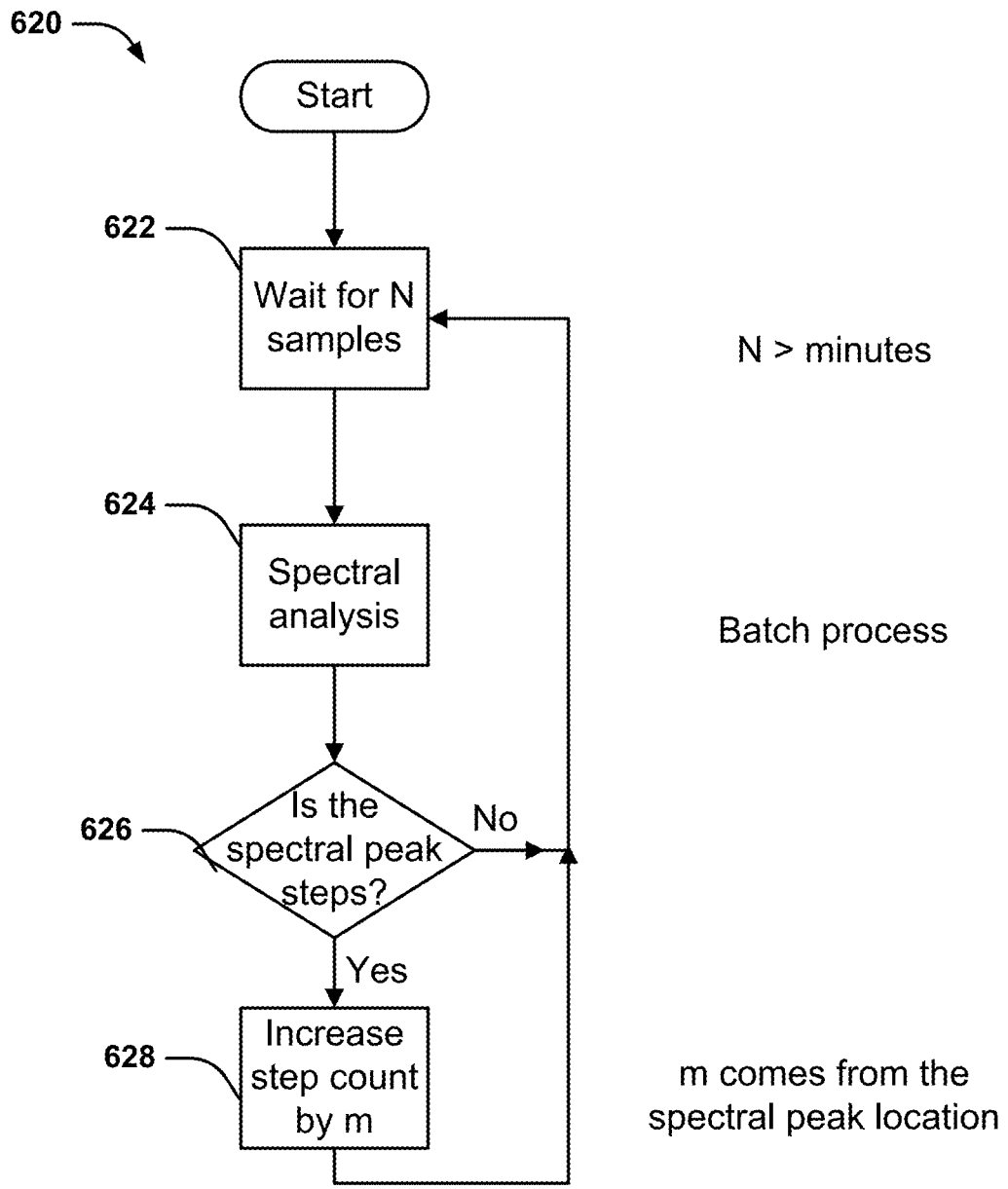
FIG. 6C is a flowchart showing a process for analyzing data in frequency domain under a semi-active mode according to some embodiments.

In some embodiments, the BMD may implement the data processing under semi-active mode using process 620 shown in FIG. 6C. Process 620 starts with obtaining N new samples of motion data such as acceleration data. The N new samples in block 622 typically include more data than the sample in block 612 of process 610 for peak detection. In some embodiments, the samples include minutes' worth of data. The amount of data necessary depends on various factors as described above, and may include various amounts in various embodiments. N depends on the data duration and sampling rate, and is limited by the memory budget for step count analysis. Process 620 proceeds to perform a spectral analysis. See block 624. In some embodiments, the spectral analysis is carried out by Fourier transform (e.g., FFT) to show the power of various frequencies. Any peak on the frequency domain indicates there is periodicity in the motion data. For instance a peak at 2 Hz indicates periodic movement of 120 times per minute. Process 620 then proceeds by examining if the spectral peak corresponds to steps. See block 626. This may be performed by applying one or more filters or classifiers. If the analysis determines that the spectral peak does not correspond to steps, then the process returns to block 622 to obtain N new samples. If the analysis determines that the spectral peak indeed relates to steps. Then the process increases the step count by M, wherein M is determined from the frequency of the spectral peak and duration of the data. For instance, if the spectral peak occurs at 2 Hz, and N samples last for 60 seconds, then M would be 120 steps. In some embodiments, harmonics of the maximum peak are also analyzed to assist determination of steps.

Figure 6D:
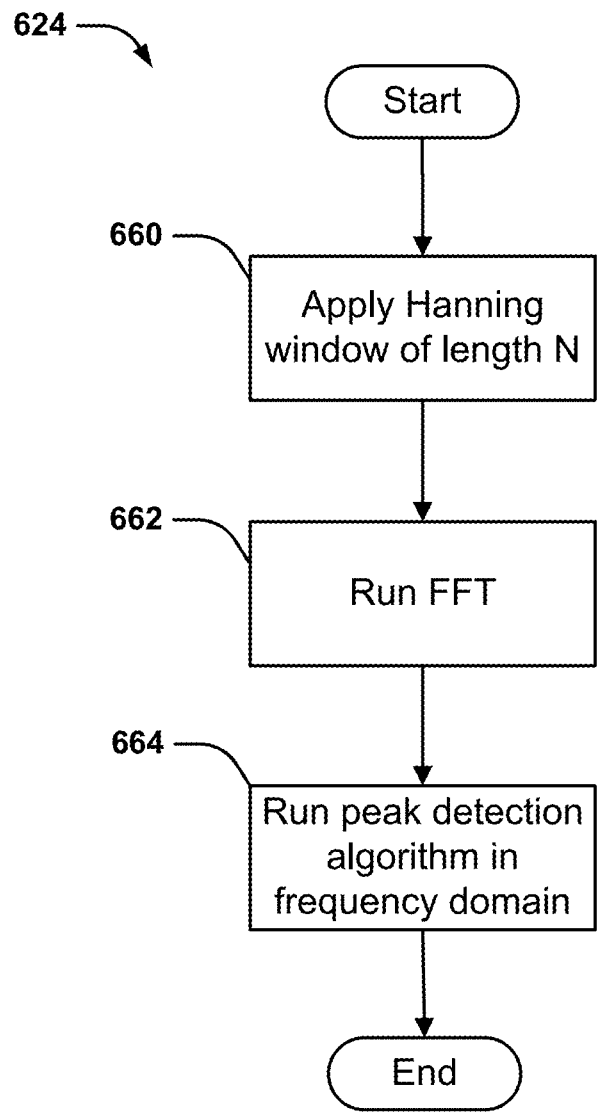
FIG. 6D is a flowchart showing a process that may be used to implement a spectral analysis according to some embodiments.

FIG. 6D shows details of a process that may be used to implement a spectral analysis applicable to operation 624 according to some embodiments. The process starts by applying a Hanning window the last for the time period of N, which prepares data for Fourier transform. See block 660. Then the process performs a fast Fourier transformation in some embodiments. See block 662. The fast Fourier transform converts time domain information into frequency domain information, showing the power of various frequencies. The process then applies the peak detection algorithm in the frequency domain to determine if there are any peaks at particular frequencies. Peak detection algorithms similar to those described above may be applied here to frequency domain data. If one or more peaks are detected for particular frequencies, the process infers that the data include a periodic component, which is used to calculate steps. For instance, if a spectral peak occurs at 1 Hz, and N samples last for 30 seconds, then the process determines that 30 steps occurs in activity providing the data.

Example-Rock Climbing Activity Type Mode

In some embodiments, NFC or other short range wireless communication such as Bluetooth, Zigbee, and/or ANT+ is used in a rock climbing setting. A climber contacts their hands and feet to climbing holds and/or climbing wall features to climb up, including the initial hold(s) and final hold(s) that define a route (a predefined area, path, and/or set of holds which can be used in a climb and is typically given a rating corresponding to its difficulty). In one embodiment, active or passive NFC enabled devices or tags are mounted on locations including but not limited to the user's hands, gloves, wrist bands feet, shoes, other body parts, wearable clothing, pocket, belt, belt loop, waistband, shirt sleeve, shirt collar, shoe, shoelaces, hat, bra, tie, sock, underwear, coin pocket, glove, other articles of clothing, accessories such as a purse, backpack, belt pack, fanny pack, goggles, swim cap, glasses, sunglasses, necklace, pendant, pin, hair accessory wristband, bracelet, upper arm band, anklet, ring, toe ring, and earring to communicate with an active or passive NFC enabled chip or device embedded in, on, or near one or more climbing holds or carabineers for sport climbing routes. The information collected by the device or devices on the climber and/or the climbing hold or wall is processed in the device or devices on the climber and/or the climbing hold or climbing wall and/or cloud computing system to provide data to the user and/or climbing gym about the user's climb.

In one embodiment, this data could be used to help the user keep track of which climbs they have completed and/or attempted. The data may also be used by the climber to remember which holds and/or climbing wall features they used and with which sequence they used the holds and/or climbing wall features. This data could be shared with other climbers to aid them in completing part or the entire climbing route, compete, earn badges and/or earn other virtual rewards. In some cases, climbers could receive only data from climbers of similar characteristics including but not limited to height, weight, experience level (e.g. years climbing), strength, confidence or fear of heights and/or flexibility so as to improve the relevance of the data in aiding them complete a climbing route. In some cases, optional holds may be virtually added or taken away from a virtual route to decrease or increase the difficulty of the route. Upon the completion of a route, the climber may have the ability to virtually share their achievement on online social networks. Virtual badges may also be awarded for reaching a climbing achievement such as completing or attempting a climb or number of climbs of a specific difficulty.

In another embodiment, climbers may wear a device which can detect freefall using, for example, a motion sensor such as an accelerometer. Freefall detection data may be communicated wirelessly to a secondary device such as a smartphone, tablet, laptop, desktop computer, or server. In one embodiment, a detection of freefall may cause an automatic braking device to prevent the rope holding the climber from falling further. This may be used in addition to or instead of automatic mechanical fall stopping mechanisms and/or manually operated fall stopping mechanisms such as a belay device.

Freefall data may also be used in determining when a rope needs to be retired from use. Metrics including but not limited to the number of free fall events, time duration of free fall, maximum acceleration, maximum force (estimated using the weight of the climber), and/or energy dissipated by the rope may be used in the calculation of when a rope should be expired. This data may also be presented to the user.

Freefall data may also be used to determine when climbers and/or belayers are climbing unsafely. For example, if a climber takes a fall of a certain magnitude (as determined by one or more freefall metrics already disclosed herein), the climbing gym staff may be alerted.

In another embodiment, climbing holds and or features may have embedded or proximal auditory and/or visual indicators. These may be used instead of the colored or patterned tape which is commonly used to indicate which hold and/or feature can be used in a climb. These indicators may also show which holds and what sequence of holds the user, one or more other users, or one or more other users of similar characteristics already disclosed herein used on a previous climb.

In another embodiment, weight sensors integrated into the holds and/or features may determine which holds and/or features were used during a climb. The sequence of holds and/or wall features may be also determined by a separate device in communication with the weight sensor enabled holds.

The climbing holds and/or wall features may also be used to determine which holds and/or wall features were used by feet, hands and/or other body parts. In one embodiment, they can also determine which hand or foot (e.g. left or right) was used on which hold.

In one embodiment, visual characteristics of the holds or wall features (e.g. color, brightness, number of illuminated LED's) may change in reaction to having been used by a climber. This may be achieved with, for example, an RGB LED mounted inside a translucent hold and/or wall feature.

The visual indicators may also be located in proximity to the hold or wall features rather than being integrated into them directly.

Biometric Monitoring Device

It is desirable to have BMD that provide accurate analyses of metrics under different measurement conditions while maintaining overall analysis speed and energy efficiency. In some embodiments, the accuracy, speed, and efficiency may be achieved by deploying multiple modes that process sensor output data differently. In some embodiments, the BMD may switch modes by automatic triggers as described above.

In some implementations, a BMD may be designed such that it may be inserted into, and removed from, a plurality of compatible cases/housings/holders, e.g., a wristband that may be worn on a person's forearm or a belt clip case that may be attached to a person's clothing. In some embodiments, the biometric monitoring system may also include other devices or components communicatively linked to the biometric monitoring device. The communicative linking may involve direct or indirect connection, as well as wired and wireless connections. Components of said system may communicate to one another over a wireless connection (e.g. Bluetooth) or a wired connection (e.g. USB). Indirect communication refers to the transmission of data between a first device and a secondary device with the aid of one or multiple intermediary third devices which relay the data.

Figure 7:
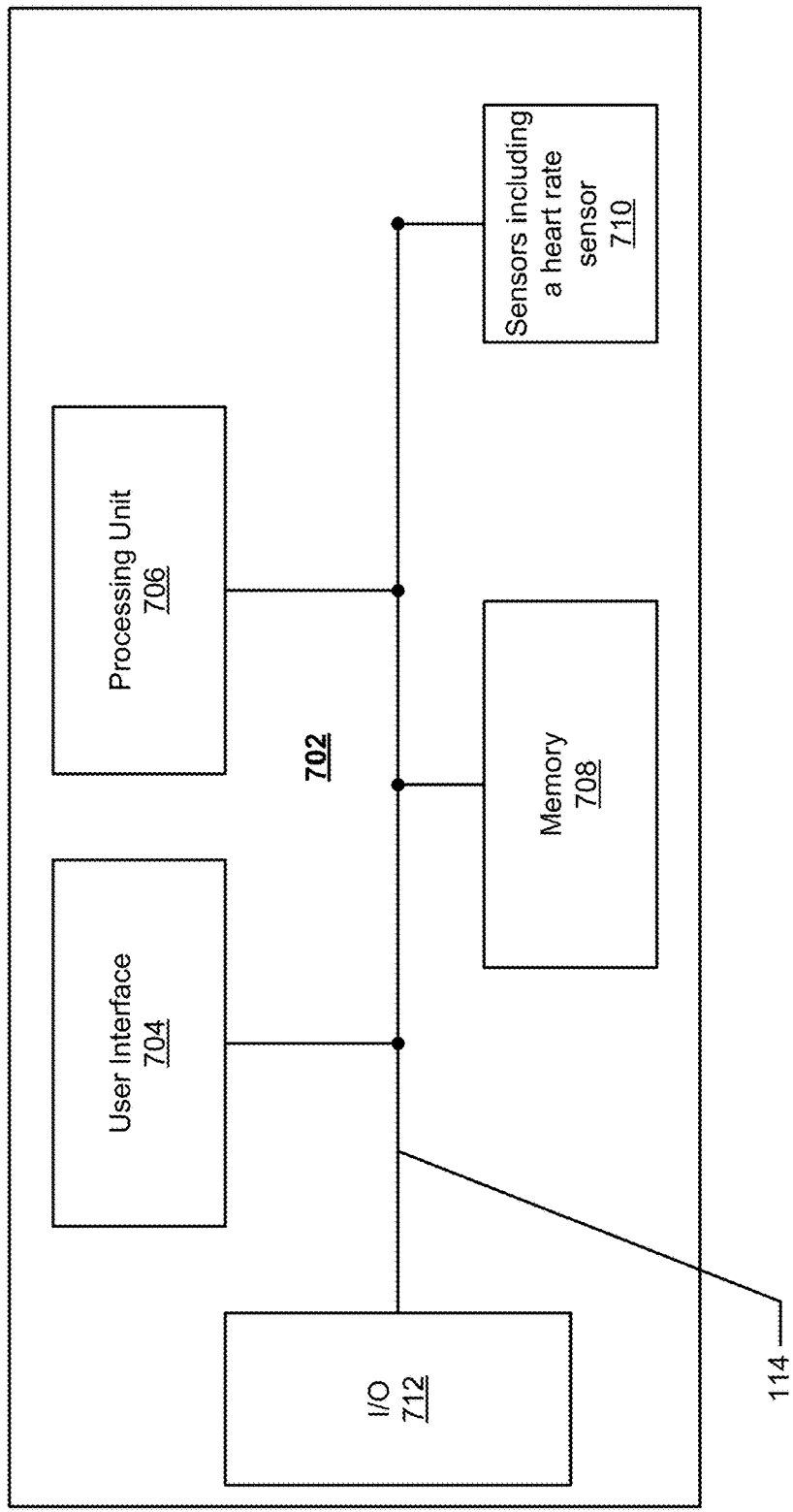
FIG. 7 depicts a generalized schematic of an example of a portable biometric monitoring device or other device that may implement the multimode functions described herein.

FIG. 7 depicts a generalized schematic of an example portable biometric monitoring device, also simply referred to herein as "biometric monitoring device," or other device with which the various operations described herein may be executed. The portable biometric monitoring device 702 may include a processing unit 706 having one or more processors, a memory 708, a user interface 704, one or more biometric sensors 710, and input/output 712. The processing unit 706, the memory 708, the user interface 704, the one or more biometric sensors 710, and the input/output interface 712 may be communicatively connected via communications path(s) 714. It is to be understood that some of these components may also be connected with one another indirectly. In some embodiments, components of FIG. 7 may be implemented as an external component communicatively linked to other internal components. For instance, in one embodiment, the memory 708 may be implemented as a memory on a secondary device such as a computer or smart phone that communicates with the device wirelessly or through wired connection via the I/O interface 712. In another embodiment, the User Interface may include some components on the device such as a button, as well as components on a secondary device communicatively linked to the device via the I/O interface 712, such as a touch screen on a smart phone.

The portable biometric monitoring device may collect one or more types of biometric data, e.g., data pertaining to physical characteristics of the human body (such as step count, heartbeat, perspiration levels, etc.) and/or data relating to the physical interaction of that body with the environment (such as accelerometer readings, gyroscope readings, etc.), from the one or more sensors 710 and/or external devices (such as an external blood pressure monitor). In some embodiments, the device stores collected information in memory 708 for later use, e.g., for communication to another device via the I/O interface 712, e.g., a smartphone or to a server over a wide-area network such as the Internet.

Biometric information, as used herein, refers to information relating to the measurement and analysis of physical or behavioral characteristics of human or animal subjects. Some biometric information describes the relation between the subject and the external environment, such as altitude or course of a subject. Other biometric information describes the subject's physical condition without regard to the external environment, such as the subject's step count or heart rate. The information concerning the subject is generally referred to as biometric information. Similarly, sensors for collecting the biometric information are referred to herein as biometric sensors. In contrast, information about the external environment regardless of the subject's condition is referred to as environmental information, and sensors for collecting such information are referred to herein as environmental sensors. It is worth noting that sometimes the same sensor may be used to obtain both biometric information and environmental information. For instance, a light sensor worn by the user may function as part of a photoplethysmography (PPG) sensor that gathers biometric information based on the reflection of light from the subject (such light may originate from a light source in the device that is configured to illuminate the portion of the person that reflects the light). The same light sensor may also gather information regarding ambient light when the device is not illuminating the portion of the person. In this disclosure, the distinctions between biometric and non-biometric information and sensors are drawn for organizational purposes only. This distinction is not essential to the disclosure, unless specified otherwise.

The processing unit 706 may also perform an analysis on the stored data and may initiate various actions depending on the analysis. For example, the processing unit 706 may determine that the data stored in the memory 708 indicates that a goal step-count or cadence has been reached and may then display content on a display of the portable BMD celebrating the achievement of the goal. The display may be part of the user interface 704 (as may be a button or other control, not pictured, that may be used to control a functional aspect of the portable biometric monitoring device). In some embodiments, the user interface 704 includes components in or on the device. In some embodiments, the user interface 704 also includes components external from the device that are nonetheless communicatively linked to the device. For instance, a smartphone or a computer communicatively linked to the BMD may provide user interface components through which a user can interact with the BMD.

In general, BMDs may incorporate one or more types of user interfaces including but not limited to visual, auditory, touch/vibration, or combinations thereof. The BMD may, for example, display information relating to one or more of the data types available and/or being tracked by the biometric monitoring device through, for example, a graphical display or through the intensity and/or color of one or more LEDs. The user interface may also be used to display data from other devices or internet sources. The device may also provide haptic feedback through, for instance, the vibration of a motor or a change in texture or shape of the device. In some implementations, the biometric sensors themselves may be used as part of the user interface, e.g., accelerometer sensors may be used to detect when a person taps the housing of the biometric monitoring unit with a finger or other object and may then interpret such data as a user input for the purposes of controlling the biometric monitoring device.

The biometric monitoring device may include one or more mechanisms for interacting with the device either locally or remotely. In one embodiment, the biometric monitoring device may convey data visually through a digital display. The physical embodiment of this display may use any one or a plurality of display technologies including, but not limited to one or more of LED, LCD, AMOLED, E-Ink, Sharp display technology, graphical display, and other display technologies such as TN, HTN, STN, FSTN, TFT, IPS, and OLET. This display could show data acquired or stored locally on the device or could display data acquired remotely from other devices or Internet services. The device may use a sensor (for example, an Ambient Light Sensor, "ALS") to control or adjust screen backlighting. For example, in dark lighting situations, the display may be dimmed to conserve battery life, whereas in bright lighting situations, the display may increase its brightness so that it is more easily read by the user.

In another embodiment, the device may use single or multicolor LEDs to indicate a state of the device. States that the device indicate may include but are not limited to biometric states such as heart rate or application states such as an incoming message, a goal has been reached. These states may be indicated through the LED's color, being on, off, an intermediate intensity, pulsing (and/or rate thereof), and/or a pattern of light intensities from completely off to highest brightness. In one embodiment, an LED may modulate its intensity and/or color with the user's cadence or step count.

In one embodiment, the use of an E-Ink display would allow the display to remain on without the battery drain of a non-reflective display. This "always-on" functionality may provide a pleasant user experience in the case of, for example, a watch application where the user may simply glance at the device to see the time. The E-Ink display always displays content without comprising the battery life of the device, allowing the user to see the time as they would on a traditional watch.

The device may use a light such as an LED to display the step count or heart rate of the user by modulating the amplitude of the light emitted at the frequency of the user's steps or heart rate. The device may be integrated or incorporated into another device or structure, for example, glasses or goggles, or communicate with glasses or goggles to display this information to the user.

The biometric monitoring device may also convey information to a user through the physical motion of the device. One such embodiment of a method to physically move the device is the use of a vibration inducing motor. The device may use this method alone, or in combination with a plurality of motion inducing technologies.

The device may convey information to a user through audio. A speaker could convey information through the use of audio tones, voice, songs, or other sounds.

Another embodiment the biometric monitoring device may transmit and receive data and/or commands to and/or from a secondary electronic device. The secondary electronic device may be in direct or indirect communication with the biometric monitoring device. Direct communication refers herein to the transmission of data between a first device and a secondary device without any intermediary devices. For example, two devices may communicate to one another over a wireless connection (e.g. Bluetooth) or a wired connection (e.g. USB). Indirect communication refers to the transmission of data between a first device and a secondary device with the aid of one or multiple intermediary third devices which relay the data. Third devices may include but are not limited to a wireless repeater (e.g. WiFi repeater), a computing device such as a smartphone, laptop, desktop or tablet computer, a cell phone tower, a computer server, and other networking electronics. For example, a biometric device may send data to a smartphone which forwards the data through a cellular network data connection to a server which is connected through the internet to the cellular network.

In one embodiment, the secondary device which acts as a user interface to the biometric monitoring device may consist of a smartphone. An app on the smart phone may facilitate and/or enable the smartphone to act as a user interface to the biometric monitoring device. The biometric monitoring device may send biometric and other data to the smartphone in real-time or with some delay. The smart phone may send a command or commands to the biometric device for example to instruct it to send biometric and other data in real-time or with some delay.

The smartphone may have one or multiple apps to enable the user to view data from their biometric device or devices. The app may by default open to a "dashboard" page when the user launches or opens the app. On this page, summaries of data totals such as heart rate, the total number of steps, floors climbed miles traveled, calories burned, calories consumed and water consumed may be shown. Other pertinent information such as when the last time the app received data from the biometric monitoring device, metrics regarding the previous night's sleep (e.g. when the user went to sleep, woke up, and how long they slept for), and how many calories the user can eat in the day to maintain their caloric goals (e.g. a calorie deficit goal to enable weight loss) may also be shown. The user may be able to choose which of these and other metrics are shown on the dashboard screen. The user may be able to see these and other metrics on the dashboard for previous days. They may be able to access previous days by pressing a button or icon on a touchscreen. Alternatively, gestures such as swiping to the left or right may enable the user to navigate through current and previous metrics.

The biometric monitoring device may be configured to communicate with the user through one or more feedback mechanisms, or combinations thereof, such as vibratory feedback, audio output, graphical output via a display or light-emitting devices, e.g., LEDs.

In one example, while the user is wearing the biometric monitoring device 702, the biometric monitoring device 702 may measure and store a user's step count or heart rate while the user is wearing the biometric monitoring device 702 and then subsequently transmit data representative of step count or heart rate to the user's account on a web service like fitbit dot com, to a mobile computational device, e.g., a phone, paired with the portable biometric monitoring unit, and/or to a standalone computer where the data may be stored, processed, and visualized by the user. Such data transmission may be carried out via communications through I/O interface 712. The device may measure, calculate, or use a plurality of physiological metrics including, but not limited to, step count, heart rate, caloric energy expenditure, floors climbed or descended, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, and respiration rate. Some of this data may be provided to the biometric monitoring device from an external source, e.g., the user may input their height, weight, and stride in a user profile on a fitness-tracking website and such information may then be communicated to the biometric monitoring device via the I/O interface 712 and used to evaluate, in tandem with data measured by the sensors 710, the distance traveled or calories burned by the user. The device may also measure or calculate metrics related to the environment around the user such as barometric pressure, weather conditions, light exposure, noise exposure, and magnetic field.

As mentioned previously, collected biometric data from the biometric monitoring device may be communicated to external devices through the communications or I/O interface 712. The I/O or communications interface may include wireless communication functionality so that when the biometric monitoring device comes within range of a wireless base station or access point, the stored data automatically uploads to an Internet-viewable source such as a website, e.g., fitbit dot com. The wireless communications functionality may be provided using one or more communications technologies known in the art, e.g., Bluetooth, RFID, Near-Field Communications (NFC), Zigbee, Ant, optical data transmission, etc. The biometric monitoring device may also contain wired communication capability, e.g., USB.

Other implementations regarding the use of short range wireless communication are described in U.S. patent application Ser. No. 13/785,904, titled "Near Field Communication System, and Method of Operating Same" filed Mar. 5, 2013 which is hereby incorporated herein by reference in its entirety.

It is to be understood that FIG. 7 illustrates a generalized implementation of a biometric monitoring device 702 that may be used to implement a portable biometric monitoring device or other device in which the various operations described herein may be executed. It is to be understood that in some implementations, the functionality represented in FIG. 7 may be provided in a distributed manner between, for example, an external sensor device and communication device, e.g., an external blood pressure meter that may communicate with a biometric monitoring device.

Moreover, it is to be understood that in addition to storing program code for execution by the processing unit to effect the various methods and techniques of the implementations described herein, the memory 708 may also store configuration data or other information used during the execution of various programs or instruction sets or used to configure the biometric monitoring device. The memory 708 may also store biometric data collected by the biometric monitoring device. In some embodiments, the memory may be distributed on more than one devices, e.g., spanning both the BMD and an external computer connected through the I/O 712. In some embodiments, the memory may be exclusively located on an external device. With regard to the memory architecture, for example, multiple different classes of storage may be provided within the memory 708 to store different classes of data. For example, the memory 708 may include non-volatile storage media such as fixed or removable magnetic, optical, or semiconductor-based media to store executable code and related data and/or volatile storage media such as static or dynamic RAM to store more transient information and other variable data.

It is to be further understood that the processing unit 706 may be implemented by a general or special purpose processor (or set of processing cores) and thus may execute sequences of programmed instructions to effectuate the various operations associated with sensor device syncing, as well as interaction with a user, system operator or other system components. In some implementations, the processing unit may be an application-specific integrated circuit.

Though not shown, numerous other functional blocks may be provided as part of the biometric monitoring device 702 according to other functions it may be required to perform, e.g., environmental sensing functionality, etc. Other functional blocks may provide wireless telephony operations with respect to a smartphone and/or wireless network access to a mobile computing device, e.g., a smartphone, tablet computer, laptop computer, etc. The functional blocks of the biometric monitoring device 702 are depicted as being coupled by the communication path 714 which may include any number of shared or dedicated buses or signaling links. More generally, however, the functional blocks shown may be interconnected using a variety of different architectures and may be implemented using a variety of different underlying technologies and architectures. The various methods and techniques disclosed herein may be implemented through execution of one or more a sequences of instructions, e.g., software programs, by the processing unit 706 or by a custom-built hardware ASIC (application-specific integrated circuit) or programmed into a programmable hardware device such as an FPGA (field-programmable gate array), or any combination thereof within or external to the processing unit 706.

Further implementations of portable biometric monitoring devices can be found in U.S. patent application Ser. No. 13/156,304, titled "Portable Biometric Monitoring Devices and Methods of Operating Same" filed Jun. 8, 2011, which is hereby incorporated herein by reference in its entirety.

In some implementations, the biometric monitoring device may include computer-executable instructions for controlling one or more processors of the biometric monitoring device to obtain biometric data from one or more biometric sensors. The instructions may also control the one or more processors to receive a request, e.g., an input from a button or touch interface on the biometric monitoring device, a particular pattern of biometric sensor data (e.g., a double-tap reading), etc., to display an aspect of the obtained biometric data on a display of the biometric monitoring device. The aspect may be a numerical quantity, a graphic, or simply an indicator (a goal progress indicator, for example). In some implementations, the display may be an illuminable display so as to be visible when displaying data but otherwise invisible to a casual observer. The instructions may also cause the one or more processors to cause the display to turn on from an off state in order to display the aspect of the biometric data. The instructions may also cause the display to turn off from an on state after a predefined time period elapses without any user interaction with the biometric monitoring device; this may assist in conserving power.

In some implementations, one or more components of 702 may be distributed across multiple devices, forming a biometric monitoring system 702 spanning multiple devices. Such implementations are also considered to be within the scope of this disclosure. For instance, the user interface 704 on a first device may not have any mechanism for receiving physical input from a wearer, but the user interface 704 may include a component on a second, paired device, e.g., a smart phone, that communicates wirelessly with the first device. The user interface 704 on the smart phone allows a user to provide input to the first device, such as providing user names and current location. Similarly, in some implementations, a biometric monitoring device may not have any display at all, i.e., be unable to display any biometric data directly—biometric data from such biometric monitoring devices may instead be communicated to a paired electronic device, e.g., a smartphone, wirelessly and such biometric data may then be displayed on data display screens shown on the paired electronic device. Such implementations are also considered to be within the scope of this disclosure, i.e., such a paired electronic device may act as a component of the biometric monitoring system 702 configured to communicate with biometric sensors located internal or external to the paired electronic device (such biometric sensors may be located in a separate module worn elsewhere on the wearer's body).

Biometric Sensors

In some embodiments, the biometric monitoring devices discussed herein may collect one or more types of physiological and/or environmental data from sensors embedded within the biometric monitoring devices, e.g., one or more sensors selected from the group including accelerometers, heart rate sensor, gyroscopes, altimeters, etc., and/or external devices, e.g., an external blood pressure monitor, and may communicate or relay such information to other devices, including devices capable of serving as an Internet-accessible data sources, thus permitting the collected data to be viewed, for example, using a web browser or network-based application. For example, while the user is wearing a biometric monitoring device, the device may calculate and store the user's step count using one or more sensors. The device may then transmit the data representative of the user's step count to an account on a web service, e.g., fitbit dot com, a computer, a mobile phone, or a health station where the data may be stored, processed, and visualized by the user. Indeed, the device may measure or calculate a plurality of other physiological metrics in addition to, or in place of, the user's step count or heart rate.

The measured physiological metrics may include, but are not limited to, energy expenditure, e.g., calorie burn, floors climbed and/or descended, step count, heart rate, heart rate variability, heart rate recovery, location and/or heading, e.g., via GPS, elevation, ambulatory speed and/or distance traveled, swimming lap count, bicycle distance and/or speed, blood pressure, blood glucose, skin conduction, skin and/or body temperature, electromyography data, electroencephalography data, weight, body fat, caloric intake, nutritional intake from food, medication intake, sleep periods, sleep phases, sleep quality and/or duration, pH levels, hydration levels, and respiration rate. The device may also measure or calculate metrics related to the environment around the user such as barometric pressure, weather conditions, e.g., temperature, humidity, pollen count, air quality, rain/snow conditions, wind speed, light exposure, e.g., ambient light, UV light exposure, time and/or duration spent in darkness, noise exposure, radiation exposure, and magnetic field. Furthermore, the biometric monitoring device, or an external system receiving data from the biometric monitoring device, may calculate metrics derived from the data collected by the biometric monitoring device. For instance, the device may derive one or more of the following from heart rate data: average heart rate, minimum heart rate, maximum heart rate, heart rate variability, heart rate relative to target heart rate zone, heart rate relative to resting heart rate, change in heart rate, decrease in heart rate, increase in heart rate, training advice with reference to heart rate, and a medical condition with reference to heart rate. Some of the derived information is based on both the heart rate information and other information provided by the user (e.g., age and gender) or by other sensors (elevation and skin conductance).

The biometric sensors may include one or more sensors that evaluate a physiological aspect of a wearer of the device, e.g., heart rate sensors, galvanized skin response sensors, skin temperature sensors, electromyography sensors, etc. The biometric sensors may also or alternatively include sensors that measure physical environmental characteristics that reflect how the wearer of the device is interacting with the surrounding environment, e.g., accelerometers, altimeters, GPS devices, gyroscopes, etc. All of these are biometric sensors that may all be used to gain insight into the activities of the wearer, e.g., by tracking movement, acceleration, rotations, orientation, altitude, etc.

A list of potential biometric sensor types and/or biometric data types is shown below in Table 1, including motion and heart rate sensors. This listing is not exclusive, and other types of biometric sensors other than those listed may be used. Moreover, the data that is potentially derivable from the listed biometric sensors may also be derived, either in whole or in part, from other biometric sensors. For example, an evaluation of stairs climbed may involve evaluating altimeter data to determine altitude change, clock data to determine how quickly the altitude changed, and accelerometer data to determine whether biometric monitoring device is being worn by a person who is walking (as opposed to standing still).

TABLE 1

| Biometric Sensors and Data (physiological and/or environmental) | | |
|---|---|---|
| Biometric Sensor Type | Biometric data potentially measured | Potentially derivable biometric data |
| Accelerometers | Accelerations experienced at location worn | Rotation, translation, velocity/speed, distance traveled, steps taken, elevation gained, fall indications, calories burned (in combination with data such as user weight, stride, etc.) |
| Gyroscopes | Angular orientation, angular velocity, angular acceleration and/or rotation | Rotation, orientation |
| Altimeters | Barometric pressure, temperature (to calculate a more accurate altitude) | Altitude change, flights of stairs climbed, local pressure changes, submersion in liquid |
| Pulse Oximeters | Blood oxygen saturation (SpO2), heart rate, blood volume | Heart rate variability, stress levels, active heart rate, resting heart rate, sleeping heart rate, sedentary heart rate, cardiac arrhythmia, cardiac arrest, pulse transit time, heart rate recovery time, blood volume |
| Galvanic Skin Response Sensors | Electrical conductance of skin | Perspiration, stress levels, exertion/arousal levels |
| Global Positioning System (GPS)* | Location, elevation, speed, heading | Distance traveled, velocity/speed |
| Electromyographic Sensors | Electrical pulses | Muscle tension/extension |

TABLE 1-continued

Biometric Sensors and Data (physiological and/or environmental)

| Biometric Sensor Type | Biometric data potentially measured | Potentially derivable biometric data |
|---|---|---|
| Audio Sensors | Local environmental sound levels | Laugh detection, breathing detection, snoring detection, respiration type (snoring, breathing, labored breathing, gasping), voice detection, typing detection |
| Photo/Light Sensors | Ambient light intensity, ambient light wavelength | Day/night, sleep, UV exposure, TV watching, indoor v. outdoor environment |
| Temperature Sensors | Temperature | Body temperature, ambient environment temperature |
| Strain Gauge Sensors | Weight (the strain gauges may be located in a device remote from the biometric monitoring device, e.g., a Fitbit ARIA ™ scale, and communicate weight-related data to the biometric monitoring device, either directly or via a shared account over the Internet) | Body Mass Index (BMI) (in conjunction with user-supplied height and gender information, for example) |
| Bioelectrical Impedance Sensors | Body fat percentage (may be included in remote device, such as ARIA ™ scale) | |
| Respiration Rate Sensors | Respiration rate | Sleep apnea detection |
| Blood Pressure Sensors | Systolic blood pressure, diastolic blood pressure | |
| Heart Rate Sensors | Heart rate | |
| Blood Glucose Sensors | Blood glucose levels | |
| Moisture Sensors | Moisture levels | Whether user is swimming, showering, bathing, etc. |

In addition to the above, some biometric data may be calculated by the biometric monitoring device without direct reference data obtained from the biometric sensors. For example, a person's basal metabolic rate, which is a measure of the "default" caloric expenditure that a person experiences throughout the day while at rest (in other words, simply to provide energy for basic bodily functions such as breathing, circulating blood, etc.), may be calculated based on data entered by the user and then used, in conjunction with data from an internal clock indicating the time of day, to determine how many calories have been expended by a person thus far in the day just to provide energy for basic bodily functions.

Physiological Sensors

As mentioned above, some biometric sensors can collect physiological data, others can collect environmental data, and some may collect both types of data. An optical sensor is an example of a sensor that may collect both types of data. Many of the following sensors and data overlap with the biometric sensors and data presented above. They are organized and presented below to indicate the physiological and environmental sources of information.

The biometric monitoring device of the present disclosure may use one, some or all of the following sensors to acquire physiological data, including the physiological data outlined in Table 2 below. All combinations and permutations of physiological sensors and/or physiological data are intended to fall within the scope of the present inventions. The biometric monitoring device of the present inventions may include but is not limited to one, some or all of sensors specified below to acquire the corresponding physiological data; indeed, other type(s) of sensors may be employed to acquire the corresponding physiological data, which are intended to fall within the scope of the present inventions. Additionally, the device may derive the physiological data from the corresponding sensor output data, but is not limited to the number or types of physiological data that it could derive from said sensor.

TABLE 2

Physiological Sensors and Data

| Physiological Sensors | Physiological data acquired |
|---|---|
| Optical Reflectometer Potential embodiments: Light emitter and receiver Multi or single LED and photo diode arrangement Wavelength tuned for specific physiological signals Synchronous detection/amplitude modulation | Heart Rate, Heart Rate Variability SpO2 (Saturation of Peripheral Oxygen) Respiration Stress Blood pressure Arterial Stiffness Blood glucose levels Blood volume Heart rate recovery Cardiac health |
| Motion Detector | Activity level detection |

TABLE 2-continued

Physiological Sensors and Data

| Physiological Sensors | Physiological data acquired |
|---|---|
| Potential embodiments: | Sitting/standing detection |
| Inertial, Gyro or Accelerometer | Fall detection |
| GPS | |
| Skin Temp | Stress |
| EMG | Muscle tension |
| EKG | Heart Rate, Heart Rate Variability, Heart Rate |
| Potential Embodiments: | Recovery |
| 1 lead | Stress |
| 2 lead | Cardiac health |
| Magnetometer | Activity level based on rotation |
| Laser Doppler | Blood flow |
| Power Meter | |
| Ultra Sound | Blood flow |
| Audio | Heart Rate, Heart Rate Variability, Heart Rate |
| | Recovery |
| | Laugh detection |
| | Respiration |
| | Respiration type - snoring, breathing, breathing problems |
| | User's voice |
| Strain gauge | Heart Rate, Heart Rate Variability |
| Potential embodiment: | Stress |
| In a wrist band | |
| Wet or Humidity sensor | Stress |
| Potential embodiment: | Swimming detection |
| galvanic skin response | Shower detection |

In one exemplary embodiment, the biometric monitoring device includes an optical sensor to detect, sense, sample, and/or generate data that may be used to determine information representative of heart rate. In addition, the optical sensor may optionally provide data for determining stress (or level thereof) and/or blood pressure of a user. In one embodiment, the biometric monitoring device includes an optical sensor having one or more light sources (LED, laser, etc.) to emit or output light into the user's body and/or light detectors (photodiodes, phototransistors, etc.) to sample, measure and/or detect a response or reflection and provide data used to determine data which is representative of heart rate (e.g., using photoplethysmography (PPG)), stress (or level thereof), and/or blood pressure of a user.

Environmental Sensors

The biometric monitoring device of the present inventions may use one, some or all of the following environmental sensors to, for example, acquire the environmental data, including environmental data outlined in Table 3 below. The biometric monitoring device is not limited to the number or types of sensors specified below but may employ other sensors that acquire environmental data outlined in the table below. All combinations and permutations of environmental sensors and/or environmental data are intended to fall within the scope of the present inventions. Additionally, the device may derive environmental data from the corresponding sensor output data, but is not limited to the types of environmental data that it could derive from said sensor.

The biometric monitoring device of the present inventions may use one or more, or all of the environmental sensors described herein and one or more, or all of the physiological sensors described herein. Indeed, biometric monitoring device of the present inventions may acquire any or all of the environmental data and physiological data described herein using any sensor now known or later developed—all of which are intended to fall within the scope of the present inventions.

TABLE 3

Environmental Sensors and Data

| Environmental Sensors | Environmental data acquired |
|---|---|
| Motion Detector | Location |
| Potential Embodiments: | Course |
| Inertial, Gyro or Accelerometer GPS | Heading |
| Pressure/Altimeter sensor | Elevation, elevation |
| Ambient Temp | Temperature |
| Light Sensor | Indoor vs outdoor |
| | Watching TV (spectrum/flicker rate detection) |
| | Optical data transfer - initiation, QR codes, etc. |
| | ultraviolet light exposure |
| Audio | Indoor vs. Outdoor |
| Compass | Heading |
| Potential Embodiments: | |
| 3 Axis Compass | |

In one embodiment, the biometric monitoring device may include an altimeter sensor, for example, disposed or located in the interior of the device housing. In such a case, the device housing may have a vent that allows the interior of the device to measure, detect, sample and/or experience any changes in exterior pressure. In one embodiment, the vent prevents water from entering the device while facilitating measuring, detecting and/or sampling changes in pressure via the altimeter sensor. For example, an exterior surface of the biometric monitoring device may include a vent type configuration or architecture (for example, a GORE™ vent) which allows ambient air to move in and out of the housing of the device (which allows the altimeter sensor to measure, detect and/or sample changes in pressure), but reduces, prevents and/or minimizes water and other liquids flow into the housing of the device.

The altimeter sensor, in one embodiment, may be filled with gel that allows the sensor to experience pressure changes outside of the gel. The use of a gel filled altimeter may give the device a higher level of environmental protection with or without the use of an environmentally sealed vent. The device may have a higher survivability rate with a gel filled altimeter in locations including but not limited to those that have high humidity, a clothes washer, a dish washer, a clothes dryer, a steam room, the shower, a pool, and any location where the device may be exposed to moisture, exposed to liquid or submerged in liquid.

Generally speaking, the techniques and functions outlined above may be implemented in a biometric monitoring device as machine-readable instruction sets, either as software stored in memory, as application-specific integrated circuits, field-programmable gate-arrays, or other mechanisms for providing system control. Such instruction sets may be provided to a processor or processors of a biometric monitoring device to cause the processor or processors to control other aspects of the biometric monitoring device to provide the functionality described above.

Unless the context (where the term "context" is used per its typical, general definition) of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein.

There are many concepts and implementations described and illustrated herein. While certain features, attributes and advantages of the implementations discussed herein have been described and illustrated, it should be understood that many others, as well as different and/or similar implementations, features, attributes and advantages of the present inventions, are apparent from the description and illustrations. As such, the above implementations are merely exemplary. They are not intended to be exhaustive or to limit the disclosure to the precise forms, techniques, materials and/or configurations disclosed. Many modifications and variations are possible in light of this disclosure. It is to be understood that other implementations may be utilized and operational changes may be made without departing from the scope of the present disclosure. As such, the scope of the disclosure is not limited solely to the description above because the description of the above implementations has been presented for the purposes of illustration and description.

Importantly, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

What is claimed is:

1. A biometric monitoring device comprising:
one or more motion sensors providing sensor output data comprising information about a user's motion;
a display device configured to display a step count metric generated for the user; and
one or more processors configured to:
(a) operate the one or more motion sensors when the biometric monitoring device is in motion;
(b) obtain a first set of motion sensor output data generated by the one or more motion sensors indicative of the motion of the biometric monitoring device;
(c) determine that a first signal strength of the first set of motion sensor output data is larger than a threshold value;
(d) select, based on determining that the first signal strength of the first set of motion sensor output data is larger than the threshold value, a time domain analysis of the first set of motion sensor output data over a frequency domain analysis of the first set of motion sensor output data;
(e) quantify a step count using the time domain analysis of the first set of motion sensor output data, and update the step count metric using the step count quantified using the time domain analysis of the first set of motion sensor output data;
(f) obtain a second set of motion sensor output data generated by the one or more motion sensors indicative of the motion of the biometric monitoring device;
(g) determine that a second signal strength of the second set of motion sensor output data is smaller than the threshold value;
(h) select, based on determining that the second signal strength of the second set of motion sensor output data is smaller than the threshold value, the frequency domain analysis of the second set of motion sensor output data over the time domain analysis of the second set of motion sensor output data; and
(i) quantify a step count using the frequency domain analysis of the second set of motion sensor output data, and update the step count metric using the step count quantified using the frequency domain analysis of the second set of motion sensor output data;
(j) control the display device of the biometric monitoring device to display the step count metric.

2. The biometric monitoring device of claim 1, wherein the frequency domain analysis requires more computation per unit of duration of motion sensor output data than the time domain analysis.

3. The biometric monitoring device of claim 1, wherein the frequency domain analysis requires more computation per unit of the step count metric than the time domain analysis.

4. The biometric monitoring device of claim 1, wherein the first set of motion sensor output data and the second set of motion sensor output data comprise raw data directly obtained from the one or more motion sensors without preprocessing and/or data derived from the raw data after preprocessing.

5. The biometric monitoring device of claim 1, wherein the biometric monitoring device comprises a wrist-worn biometric monitoring device or an arm-worn biometric monitoring device.

6. The biometric monitoring device of claim 1, wherein the first signal strength is a signal power or a signal-to-noise ratio of the first set of motion sensor output data.

7. The biometric monitoring device of claim 1, wherein the second signal strength is a signal power or a signal-to-noise ratio of the second set of motion sensor output data.

8. The biometric monitoring device of claim 1, wherein the first set of motion sensor output data comprises data from only one axis of a multi-axis motion sensor, and wherein the second set of motion sensor output data comprises data from two or more axes of the multi-axis motion sensor.

9. The biometric monitoring device of claim 1, wherein the first set of motion sensor output data is caused by a free motion of a limb wearing the biometric monitoring device.

10. The biometric monitoring device of claim 1, wherein the second set of motion sensor output data is caused by a reduced motion of a limb wearing the biometric monitoring device.

11. The biometric monitoring device of claim 10, wherein the reduced motion of the limb is produced when the user is holding a steady object with the limb wearing the biometric monitoring device.

12. The biometric monitoring device of claim 1, wherein the frequency domain analysis comprises: a Fourier transform, a cepstral transform, a wavelet transform, a filterbank analysis, a power spectral density analysis and/or a periodogram analysis.

13. The biometric monitoring device of claim 1, wherein the frequency domain analysis comprises filtering a time domain signal with a frequency band pass filter, and then applying a peak detection analysis in the time domain.

14. The biometric monitoring device of claim 1, wherein the frequency domain analysis comprises finding any spectral peak/peaks that is/are a function of an average step rate.

15. The biometric monitoring device of claim 1, wherein the frequency domain analysis comprises performing a Fisher's periodicity test.

16. The biometric monitoring device of claim 1, wherein the frequency domain analysis comprises using a harmonic to estimate a period and/or a test periodicity.

17. The biometric monitoring device of claim 1, wherein the frequency domain analysis comprises performing a generalized likelihood ratio test whose parametric models incorporate a harmonicity of a motion signal.

18. The biometric monitoring device of claim 1,
wherein the time domain analysis comprises:
    identifying a periodic component from the first set of motion sensor output data; and
    quantifying a step count from the periodic component from the first set of motion sensor output data;
and wherein the frequency domain analysis comprises:
    identifying a periodic component from the second set of motion sensor output data; and
    quantifying a step count from the periodic component from the second set of motion sensor output data.

19. The biometric monitoring device of claim 1, wherein updating the step count metric in (i) comprises combining the step count quantified using the time domain analysis and the step count quantified using the frequency domain analysis.

20. The biometric monitoring device of claim 1, wherein the frequency domain analysis comprises:
    detecting a frequency component from motion sensor output data;
    determining a time duration of the motion sensor output data; and
    quantifying a step count based on the detected frequency component and the determined time duration.

* * * * *